(12) United States Patent
Frei et al.

(10) Patent No.: US 11,117,903 B2
(45) Date of Patent: Sep. 14, 2021

(54) PYRIDINE DERIVATIVES

(71) Applicant: Hoffmann-La Roche Inc., Little Falls, NJ (US)

(72) Inventors: Beat Frei, Basel (CH); Luca Gobbi, Basel (CH); Uwe Grether, Basel (CH); Fabienne Ricklin, Basel (CH); Stephan Roever, Basel (CH); Mark Rogers-Evans, Basel (CH); Didier Rombach, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/722,592

(22) Filed: Dec. 20, 2019

(65) Prior Publication Data
US 2020/0239490 A1 Jul. 30, 2020

Related U.S. Application Data

(63) Continuation of application No. PCT/EP2018/066207, filed on Jun. 19, 2018.

(30) Foreign Application Priority Data

Jun. 20, 2017 (EP) .................... 17176884

(51) Int. Cl.
| | | |
|---|---|---|
| C07D 491/107 | (2006.01) | |
| A61K 9/20 | (2006.01) | |
| A61K 9/28 | (2006.01) | |
| A61K 9/48 | (2006.01) | |
| A61K 47/12 | (2006.01) | |
| A61K 47/34 | (2017.01) | |
| C07D 213/81 | (2006.01) | |
| C07D 401/12 | (2006.01) | |
| C07D 405/12 | (2006.01) | |
| C07D 413/04 | (2006.01) | |
| C07D 413/14 | (2006.01) | |

(52) U.S. Cl.
CPC ........ *C07D 491/107* (2013.01); *A61K 9/2013* (2013.01); *A61K 9/2027* (2013.01); *A61K 9/2054* (2013.01); *A61K 9/2059* (2013.01); *A61K 9/2813* (2013.01); *A61K 9/2866* (2013.01); *A61K 9/485* (2013.01); *A61K 9/4858* (2013.01); *A61K 9/4866* (2013.01); *A61K 47/12* (2013.01); *A61K 47/34* (2013.01); *C07D 213/81* (2013.01); *C07D 401/12* (2013.01); *C07D 405/12* (2013.01); *C07D 413/04* (2013.01); *C07D 413/14* (2013.01)

(58) Field of Classification Search
CPC .................................................. C07D 491/109
USPC .......................................................... 546/256
See application file for complete search history.

(56) References Cited

U.S. PATENT DOCUMENTS

| | | |
|---|---|---|
| 9,303,012 B2 | 4/2016 | Bendels et al. |
| 9,321,727 B2 | 4/2016 | Bissantz et al. |
| 9,403,808 B2 | 8/2016 | Bissantz et al. |
| 9,409,866 B2 | 8/2016 | Grether et al. |
| 9,512,141 B2 | 12/2016 | Dhurwasulu et al. |
| 9,522,886 B2 | 12/2016 | Frei et al. |
| 10,308,659 B2 | 6/2019 | Gavelle et al. |
| 2021/0115011 A1 | 4/2021 | Gobbi et al. |
| 2021/0115012 A1 | 4/2021 | Ametamey et al. |
| 2021/0115027 A1 | 4/2021 | Ametamey et al. |

FOREIGN PATENT DOCUMENTS

| | | |
|---|---|---|
| WO | 2012/168350 A1 | 12/2012 |
| WO | 2013/060751 A1 | 5/2013 |
| WO | 2014/086705 A1 | 6/2014 |
| WO | 2014/086805 A1 | 6/2014 |
| WO | 2014/086806 A1 | 6/2014 |
| WO | 2014/086807 A1 | 6/2014 |
| WO | 2014/154612 A1 | 10/2014 |
| WO | 2015/150438 A1 | 10/2015 |
| WO | 2015/150440 A1 | 10/2015 |
| WO | 2017/097732 A1 | 6/2017 |

OTHER PUBLICATIONS

"International Preliminary Report on Patentability—PCT/EP2018/066207":pp. 1-7 (Jan. 2, 2020).
"International Search Report—PCT/EP2017/066207":pp. 1-7 (Sep. 12, 2018).
U.S. Appl. No. 16/930,013, filed Jul. 15, 2020, Olivier Gavelle et al., Phenyl Derivatives as Cannabinoid Receptor 2 Agonists.
U.S. Appl. No. 17/125,648, filed Dec. 17, 2020, Simon M. Ametamey et al., Novel Azetidine-Substituted Pyridine and Pyrazine Compounds as Inhibitors of Cannabinoid Receptor 2.

*Primary Examiner* — Taofiq A Solola
(74) *Attorney, Agent, or Firm* — Zong-Qiang Bill Tian

(57) ABSTRACT

The invention relates to compound of formula (I)

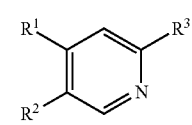

(I)

wherein $R^1$ to $R^3$ are as defined in the description and in the claims. The compound of formula (I) can be used as a medicament.

6 Claims, No Drawings

PYRIDINE DERIVATIVES

CROSS-REFERENCE TO RELATED APPLICATIONS

This application is a continuation of International Application No. PCT/EP2018/066207, filed 19 Jun. 2018, which claims benefit of priority to EP Application No. 17176884.9, filed 20 Jun. 2017, each of which is incorporated herein by reference in its entirety.

The present invention relates to organic compounds useful for therapy and/or prophylaxis in a mammal, and in particular to compounds that are preferential inverse agonists of the Cannabinoid Receptor 2.

The invention relates in particular to a compound of formula (I)

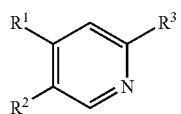

wherein $R^1$ is halophenyl, cycloalkylalkoxy, alkyloxetanylalkoxy, alkoxycarbonylpyrrolidinylalkoxy, alkoxycarbonylpyrrolidinyloxy, alkylsulfonylphenylalkoxy, haloalkoxy, (alkyl)(halo)cycloalkylalkoxy, benzotriazolyloxy, halopyridinylalkoxy or halopyridinyl;

$R^2$ is halogen, cycloalkyl, haloalkyl, cycloalkylalkoxy, 2-oxa-6-azaspiro[3.3]heptyl or phenylalkoxy;

$R^3$ is —C(O)—NH—C($R^4R^5$)$_m$(CH$_2$)$_n$—$R^6$ or alkyloxadiazolyl;

$R^4$ and $R^5$ are independently selected from hydrogen, alkyl, hydroxyalkyl, haloalkyl, azetidinyl, cycloalkylalkyl and cycloalkyl;

$R^6$ is hydroxyl, hydroxycycloalkyl, alkoxycarbonyl, alkoxycycloalkyl, aminocarbonyl, phenyl, pyridinyl, alkyl-1,2,4-oxadiazolyl, alkylaminocarbonyl, haloalkyl or alkyl-1,3,4-oxadiazolyl;

m is 0 or 1; and n is 0 or 1;

or a pharmaceutically acceptable salt or ester thereof.

The compound of formula (I) is particularly useful in the treatment or prophylaxis of pain, neuropathic pain, asthma, osteoporosis, inflammation, psychiatric diseases, psychosis, oncology, encephalitis, malaria, allergy, immunological disorders, arthritis, gastrointestinal disorders, psychiatric disorders rheumatoid arthritis, psychosis and allergy.

The cannabinoid receptors are a class of cell membrane receptors belonging to the G protein-coupled receptor superfamily. There are currently two known subtypes, termed Cannabinoid Receptor 1 (CB1) and Cannabinoid Receptor 2 (CB2). The CB1 receptor is mainly expressed in the central nervous (i.e. amygdala cerebellum, hippocampus) system and to a lesser amount in the periphery. CB2, which is encoded by the CNR2 gene, is mostly expressed peripherally, on cells of the immune system, such as macrophages and T-cells (Ashton, J. C. et al. Curr Neuropharmacol 2007, 5(2), 73-80; Miller, A. M. et al. Br J Pharmacol 2008, 153(2), 299-308; Centonze, D., et al. Curr Pharm Des 2008, 14(23), 2370-42), and in the gastrointestinal system (Wright, K. L. et al. Br J Pharmacol 2008, 153(2), 263-70). The CB2 receptor is also widely distributed in the brain where it is found primarily on microglia and not neurons (Cabral, G. A. et al. Br J Pharmacol 2008, 153(2): 240-51).

The interest in CB2 receptor ligands has been steadily on the rise during the last decade (currently 30-40 patent applications/year). Evidence from different sources support the view that lipid endocannabinoid signaling through CB2 receptors represents an aspect of the mammalian protective armamentarium (Pacher, P. Prog Lipid Res 2011, 50, 193). Its modulation by either selective CB2 receptor agonists or inverse agonists/antagonists (depending on the disease and its stage) holds unique therapeutic potential in a huge number of diseases. For CB2 inverse agonists/antagonists therapeutic opportunities have been demonstrated for many pathological conditions including pain (Pasquini, S. J Med Chem 2012, 55(11): 5391), neuropathic pain (Garcia-Gutierrez, M. S. Br J Pharmacol 2012, 165(4): 951), psychiatric disorders (Garcia-Gutierrez, M. S. Br J Pharmacol 2012, 165(4): 951), psychosis (Garcia-Gutierrez, M. S. Br J Pharmacol 2012, 165(4): 951), osteoporosis and inflammation (Sophocleous, A. Calcif Tissue Int 2008, 82(Suppl. 1):Abst OC18), psychiatric diseases and psychosis (Garcia-Gutierrez, M. S. Br J Pharmacol 2012, 165(4): 951), oncology (Preet, A. Cancer Prev Res 2011, 4:65), encephalitis and malaria (Zimmer, A. WO 2011045068), allergy and inflammation (Ueda, Y. Life Sci 2007, 80(5): 414), encephalitis and malaria (Zimmer, WO 2011045068), asthma (Lunn, C. A. J Pharmacol Exp Ther 2006, 316(2): 780), immunological disorders (Fakhfouri, G. Neuropharmacology 2012, 63(4): 653), rheumatoid arthritis (Chackalamannil, S. U.S. Pat. No. 7,776,889), arthritis (Lunn, C. A. J Pharmacol Exp Ther 2006, 316(2): 780), and gastrointestinal disorders (Barth, F. FR 2887550).

The compounds of the invention bind to and modulate the CB2 receptor and have lower CB1 receptor activity.

In the present description the term "alkyl", alone or in combination, signifies a straight-chain or branched-chain alkyl group with 1 to 8 carbon atoms, particularly a straight or branched-chain alkyl group with 1 to 6 carbon atoms and more particularly a straight or branched-chain alkyl group with 1 to 4 carbon atoms. Examples of straight-chain and branched-chain C1-C8 alkyl groups are methyl, ethyl, propyl, isopropyl, butyl, isobutyl, tert.-butyl, the isomeric pentyls, the isomeric hexyls, the isomeric heptyls and the isomeric octyls, particularly methyl, ethyl, propyl, butyl and pentyl. Particular examples of alkyl are methyl, ethyl, isopropyl, butyl, isobutyl, tert.-butyl and pentyl. Methyl, ethyl, tert-butyl and isobutyl are particular examples of alkyl in the compound of formula (I).

The term "cycloalkyl", alone or in combination, signifies a cycloalkyl ring with 3 to 8 carbon atoms and particularly a cycloalkyl ring with 3 to 6 carbon atoms. Examples of cycloalkyl are cyclopropyl, cyclobutyl, cyclopentyl and cyclohexyl, cycloheptyl and cyclooctyl. Particular examples of "cycloalkyl" are cyclopropyl and cyclohexyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec-butoxy and tert.-butoxy. Particular "alkoxy" are methoxy and tert.-butyloxy.

The term "oxy", alone or in combination, signifies the —O— group.

The term "oxo", alone or in combination, signifies the =O group.

The terms "halogen" or "halo", alone or in combination, signifies fluorine, chlorine, bromine or iodine and particularly fluorine, chlorine or bromine, more particularly fluorine and chlorine. The term "halo", in combination with another group, denotes the substitution of said group with at least one halogen, particularly substituted with one to five halogens, particularly one to four halogens, i.e. one, two, three or four halogens.

The term "haloalkyl", alone or in combination, denotes an alkyl group substituted with at least one halogen, particularly substituted with one to five halogens, particularly one to three halogens. Particular "haloalkyl" are trifluoromethyl and trifluoroethyl, in particular trifluoromethyl.

The term "haloalkoxy" or "haloalkyloxy", alone or in combination, denotes an alkoxy group substituted with at least one halogen, particularly substituted with one to five halogens, particularly one to three halogens. A Particular "haloalkoxy" is trifluoroethyloxy.

The terms "hydroxyl" and "hydroxy", alone or in combination, signify the —OH group.

The term "carbonyl", alone or in combination, signifies the —C(O)— group.

The term "amino", alone or in combination, signifies the primary amino group (—NH2), the secondary amino group (—NH—), or the tertiary amino group (—N—).

The term "aminocarbonyl", alone or in combination, signifies the —C(O)—NH$_2$, C(O)—NH— or —C(O)—NH— group.

The term "sulfonyl", alone or in combination, signifies the —SO$_2$ group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein. In addition these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins. The compound of formula (I) can also be present in the form of zwitterions. Particularly preferred pharmaceutically acceptable salts of compounds of formula (I) are the salts of hydrochloric acid, hydrobromic acid, sulfuric acid, phosphoric acid and methanesulfonic acid.

"Pharmaceutically acceptable esters" means that the compound of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compound of general formula (I), similar to the metabolically labile esters, which are capable of producing the parent compound of general formula (I) in vivo, are within the scope of this invention.

If one of the starting materials or compounds of formula (I) contain one or more functional groups which are not stable or are reactive under the reaction conditions of one or more reaction steps, appropriate protecting groups (as described e.g. in "Protective Groups in Organic Chemistry" by T. W. Greene and P. G. M. Wuts, 3rd Ed., 1999, Wiley, New York) can be introduced before the critical step applying methods well known in the art. Such protecting groups can be removed at a later stage of the synthesis using standard methods described in the literature. Examples of protecting groups are tert-butoxycarbonyl (Boc), 9-fluorenylmethyl carbamate (Fmoc), 2-trimethyl silylethyl carbamate (Teoc), carbobenzyloxy (Cbz) and p-methoxybenzyloxycarbonyl (Moz).

The compound of formula (I) can contain several asymmetric centers and can be present in the form of optically pure enantiomers, mixtures of enantiomers such as, for example, racemates, mixtures of diastereo-isomers, diastereoisomeric racemates or mixtures of diastereoisomeric racemates.

The term "asymmetric carbon atom" means a carbon atom with four different substituents. According to the Cahn-Ingold-Prelog Convention an asymmetric carbon atom can be of the "R" or "S" configuration.

The invention relates in particular to:

A compound of formula (I) wherein $R^1$ is alkoxycarbonylpyrrolidinylalkoxy, alkoxycarbonylpyrrolidinyloxy, alkylsulfonylphenylalkoxy, (alkyl)(halo)cycloalkylalkoxy, benzotriazolyloxy, halopyridinylalkoxy or halopyridinyl;

A compound of formula (I) wherein $R^1$ is tert.-butyloxycarbonylpyrrolidinylmethoxy, butyloxycarbonylpyrrolidinyloxy, methylsulfonylphenylmethoxy, (methyl)(difluoro) cyclopropylmethoxy, benzotriazolyloxy, fluoropyridinylmethoxy or fluoropyridinyl;

A compound of formula (I) wherein $R^2$ is haloalkyl, cycloalkylalkoxy, 2-oxa-6-azaspiro[3.3]heptyl or phenylalkoxy;

A compound of formula (I) wherein $R^2$ is hydrogen, trifluoromethyl, cyclopropylmethoxy, 2-oxa-6-azaspiro[3.3]heptyl or phenylmethoxy;

A compound of formula (I) wherein $R^3$ is —C(O)—NH—C(O)—NH—C($R^4R^5$)$_m$(CH$_2$)$_n$—$R^6$ or tert.-butyloxadiazolyl;

A compound of formula (I) wherein $R^6$ is hydroxyl, alkoxycarbonyl, aminocarbonyl or alkylaminocarbonyl; and A compound of formula (I) wherein $R^6$ is hydroxyl, methoxycarbonyl, aminocarbonyl or methylaminocarbonyl.

The invention further relates to a compound or formula (I) selected from:

5-(cyclopropylmethoxy)-4-(2,4-dichlorophenyl)-N-[(2S)-1-hydroxy-4-methylpentan-2-yl]pyridine-2-carboxamide;

4-(4-chlorophenyl)-5-(cyclopropylmethoxy)-N-[(1R,2S)-2-hydroxycyclohexyl]pyridine-2-carboxamide;

4-(4-chlorophenyl)-5-(cyclopropylmethoxy)-N-[(1 S,2R)-2-hydroxycyclohexyl]pyridine-2-carboxamide;

methyl 2-[[4-(4-chlorophenyl)-5-(cyclopropylmethoxy) pyridine-2-carbonyl]amino]-2-ethylbutanoate;

methyl 2-[[5-(cyclopropylmethoxy)-4-(3,4-di chlorophenyl) pyridine-2-carbonyl]amino]-2-ethylbutanoate;

4-(4-chlorophenyl)-5-(cyclopropylmethoxy)-N-[(1R,2S)-2-methoxycyclohexyl]pyridine-2-carboxamide;

5-chloro-4-(cyclopropylmethoxy)-N-[(1R)-2-hydroxy-1-phenylethyl]pyridine-2-carboxamide;

5-chloro-4-(cyclopropylmethoxy)-N-[(2S)-3,3-dimethyl-1-(methylamino)-1-oxobutan-2-yl]pyridine-2-carboxamide;

5-chloro-4-(cyclopropylmethoxy)-N-[(1S)-2,2,2-trifluoro-1-pyridin-2-ylethyl]pyridine-2-carboxamide;

5-chloro-4-(cyclopropylmethoxy)-N-[(1R)-2,2,2-trifluoro-1-pyridin-3-ylethyl]pyridine-2-carboxamide;

5-chloro-4-(cyclopropylmethoxy)-N-[(2S)-4-methyl-1-(methylamino)-1-oxopentan-2-yl]pyridine-2-carboxamide;
5-chloro-4-(cyclopropylmethoxy)-N-[(2R)-4-methyl-1-(methylamino)-1-oxopentan-2-yl]pyridine-2-carboxamide;
5-cyclopropyl-N-[(2S)-3,3-dimethyl-1-(methylamino)-1-oxobutan-2-yl]-4-[(3-methyloxetan-3-yl)methoxy]pyridine-2-carboxamide;
6-[6-(5-tert-butyl-1,2,4-oxadiazol-3-yl)-4-(cyclopropylmethoxy)pyridin-3-yl]-2-oxa-6-azaspiro[3.3]heptane;
tert-butyl (2S)-2-[[2-(5-tert-butyl-1,2,4-oxadiazol-3-yl)-5-cyclopropylpyridin-4-yl]oxymethyl]pyrrolidine-1-carboxylate;
tert-butyl (3R)-3-[2-(5-tert-butyl-1,2,4-oxadiazol-3-yl)-5-cyclopropylpyridin-4-yl]oxypyrrolidine-1-carboxylate;
5-tert-butyl-3-[5-cyclopropyl-4-[(3-methylsulfonylphenyl)methoxy]pyridin-2-yl]-1,2,4-oxadiazole;
N-[1-(azetidin-3-yl)-1-(5-methyl-1,3,4-oxadiazol-2-yl)ethyl]-5-cyclopropyl-4-(2,2,2-trifluoroethoxy)pyridine-2-carboxamide;
ethyl 2-[[5-cyclopropyl-4-[(3-methyloxetan-3-yl)methoxy]pyridine-2-carbonyl]amino]-2-ethylbutanoate;
5-chloro-N-[1-cyclopropyl-2-(5-methyl-1,2,4-oxadiazol-3-yl)propan-2-yl]-4-[(2,2-difluoro-1-methylcyclopropyl)methoxy]pyridine-2-carboxamide;
4-(benzotriazol-1-yloxy)-N-[1-cyclopropyl-2-(5-methyl-1,2,4-oxadiazol-3-yl)propan-2-yl]-5-(trifluoromethyl)pyridine-2-carboxamide;
N-(4-amino-2-cyclopropyl-4-oxobutan-2-yl)-5-cyclopropyl-4-[(5-fluoropyridin-2-yl)methoxy]pyridine-2-carboxamide; and
N-[(2S)-1-cyclopropyl-2-(5-methyl-1-1,2,4-oxadiazol-3-yl)propan-2-yl]-4-(6-fluoropyridin-3-yl)-5-phenylmethoxypyridine-2-carboxamide.

The invention further relates in particular to a compound of formula (I) selected from
5-(cyclopropylmethoxy)-4-(2,4-dichlorophenyl)-N-[(2S)-1-hydroxy-4-methylpentan-2-yl]pyridine-2-carboxamide;
methyl 2-[[5-(cyclopropylmethoxy)-4-(3,4-dichlorophenyl)pyridine-2-carbonyl]amino]-2-ethylbutanoate;
5-chloro-4-(cyclopropylmethoxy)-N-[(2S)-3,3-dimethyl-1-(methylamino)-1-oxobutan-2-yl]pyridine-2-carboxamide;
5-cyclopropyl-N-[(2S)-3,3-dimethyl-1-(methylamino)-1-oxobutan-2-yl]-4-[(3-methyloxetan-3-yl)methoxy]pyridine-2-carboxamide; and
N-(4-amino-2-cyclopropyl-4-oxobutan-2-yl)-5-cyclopropyl-4-[(5-fluoropyridin-2-yl)methoxy]pyridine-2-carboxamide.

In the following schemes and description, $R^1$ to $R^6$ have, unless otherwise indicated, the meaning of $R^1$ to $R^6$ as defined above.

The preparation of compounds of formula (I) of the present invention may be carried out in sequential or convergent synthetic routes. Syntheses of the compounds of the invention are shown in the following scheme. The skills required for carrying out the reactions and purifications of the resulting products are known to those skilled in the art. The substituents and indices used in the following description of the processes have the significance given herein before unless indicated to the contrary. In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations,* 2nd Edition, Richard C. Larock. John Wiley & Sons, New York, N.Y. 1999). We found it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux. The time required for the reaction may also vary widely, depending on many factors, notably the reaction temperature and the nature of the reagents. However, a period of from 0.5 hours to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

The synthesis of the compounds with the general structure I can, for example, be accomplished according to the following schemes.

Following the procedure according to scheme 1, compound AA (6-chloro-5-hydroxy-4-iodo-2-pyridinemethanol, CAS RN 208519-37-3) can be used as starting material. AA is commercially available or can alternatively be prepared by a two step sequence from 2-chloro-3-pyridinol following literature procedures or by other procedures known to a person skilled in the art.

Scheme 1

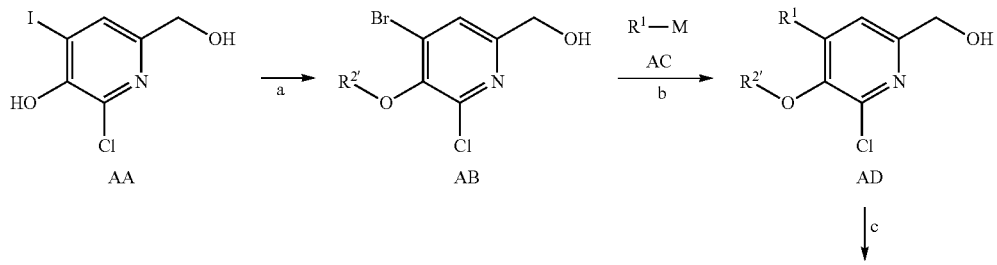

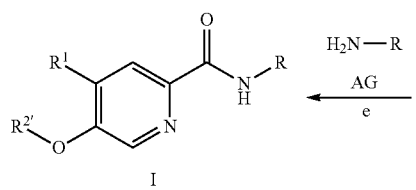 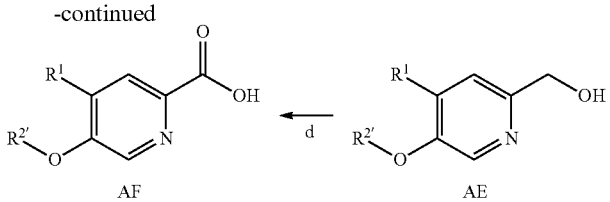

Compound AB can be prepared from AA by reaction with a suitably substituted primary or secondary alkylhalide $R^{2'}$-X or primary or secondary alkyltrifluoromethanesulfonate $R^{2'}$-OTf in the presence of a base, for example sodium hydride, in an inert solvent, for example hexamethylphosphoramide, at temperatures from room temperature to reflux temperature of the solvent, preferably at elevated temperature e.g. 120° C. ($R^{2'}$=cycloalkylalkyl or phenylalkyl; step a).

Compound AD can be prepared from AB by coupling a suitably substituted aryl metal species of formula AC, preferably an arylboronic acid or arylboronic acid ester, with AB in the presence of a suitable catalyst, preferably a palladium catalyst and more preferably palladium(II)acetate/triphenylphosphine mixtures or palladium(II)chloride-dppf (1,1'-bis(diphenylphosphino)ferrocene) complexes and a base, preferably triethylamine or sodium carbonate in an inert solvent such as dimethylformamide or toluene (step b).

Compound AE can be obtained by selective hydrogenation of compound AC by methods known in the art, for example by hydrogenation with zinc in acetic acid in the presence of tetramethylammonium bromide at temperatures from room temperature to reflux temperature of the solvent, preferably at a temperature of 50° C. (step c).

Compound AF can be prepared from AE by oxidation using the vast array of possibilities known in the art. A convenient method is the use of a TEMPO catalyzed oxidation with a sodiumchlorite-sodiumhypochlorite mixture in a suitable solvent mixture, preferably in acetonitrile/phosphate buffer mixtures, at temperatures from room temperature to elevated temperatures, preferably at 35° C. (step d).

Compound I can be prepared from acids AF and the corresponding amine AG (R=—C($R^4R^5$)$_m$(CH$_2$)$_n$—$R^6$) by suitable amide bond forming reactions. These reactions are known in the art. For example coupling reagents like N,N'-carbonyl-diimidazole (CDI), N,N'-dicyclohexylcarbodiimide (DCC), 1-(3-dimethylaminopropyl)-3-ethyl carbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), and O-benzotriazol-1-yl-N,N,N',N'-tetramethyluronium tetrafluoroborate (TBTU) can be employed to affect such transformations (step e). A convenient method is to use for example TBTU and a base, for example Hünig's base (N-ethyldiisopropylamine) in an inert solvent such as for example dimethylformamide at room temperature.

If one of the starting materials, compounds of formulae AA, AC or AG, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae AA to AC or AG contain chiral centers, compounds of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 2, compound BA (X=Cl, Br, I) can be used as starting material (e.g. 5-chloro-4-iodo-2-pyridinecarboxylic acid (CAN 120643-06-3) for a subset of compounds where $R^2$=Cl). BA is either commercially available, described in the literature, can be synthesized by a person skilled in the art or can be synthesized as described in the experimental part.

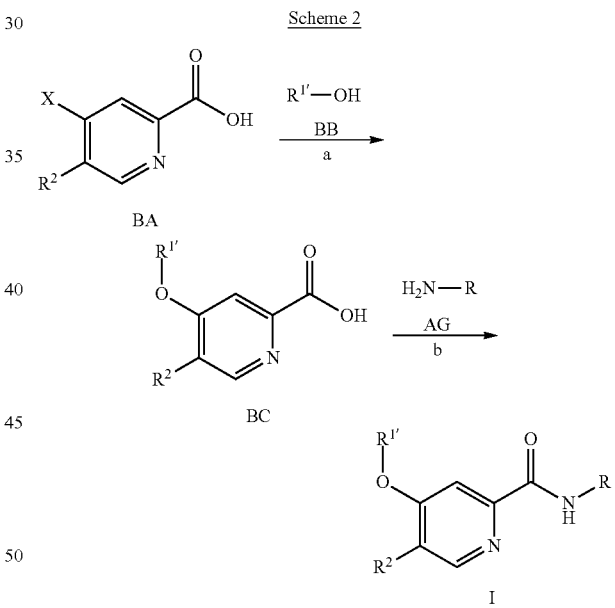

Scheme 2

Compounds BC can be prepared from BA by reaction with a suitably substituted primary or secondary alcohol BB in the presence of a base, for example potassium tert-butoxide, in an inert solvent, for example dimethylformamide or tetrahydrofurane, at temperatures ranging from room temperature to the reflux temperature of the solvent, particularly at elevated temperature as for example 80° C. (step a).

Compounds of formula I can be prepared from BC and the corresponding amine of formula AG (R=—C($R^4R^5$)$_m$ (CH$_2$)$_n$ —$R^6$) by suitable amide bond forming reactions. These reactions are known in the art. For example coupling reagents like N,N'-carbonyl-diimidazole (CDI), N,N'-dicyclohexylcarbodiimide (DCC), 1-(3-dimethylaminopropyl)-

3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N'N'-tetramethyluronium tetrafluoroborate (TBTU), and O-benzotriazole-N,N,N',N'-tetramethyl-uronium-hexafluorophosphate (HBTU) can be employed to affect such transformation (step b). A convenient method is to use for example HBTU and a base, for example DIEA in an inert solvent such as for example dimethylformamide at room temperature.

Amines AG are either commercially available, described in the literature, can be synthesized by a person skilled in the art or as described in the experimental part.

If one of the starting materials, compounds of formulae BA, BB or AG, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae BA to BB or AG contain chiral centers, compounds of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

Following the procedure according to scheme 3, compound CA can be used as starting material. CA is either commercially available, described in the literature, can be synthesized by a person skilled in the art or as described in the experimental part.

Scheme 3

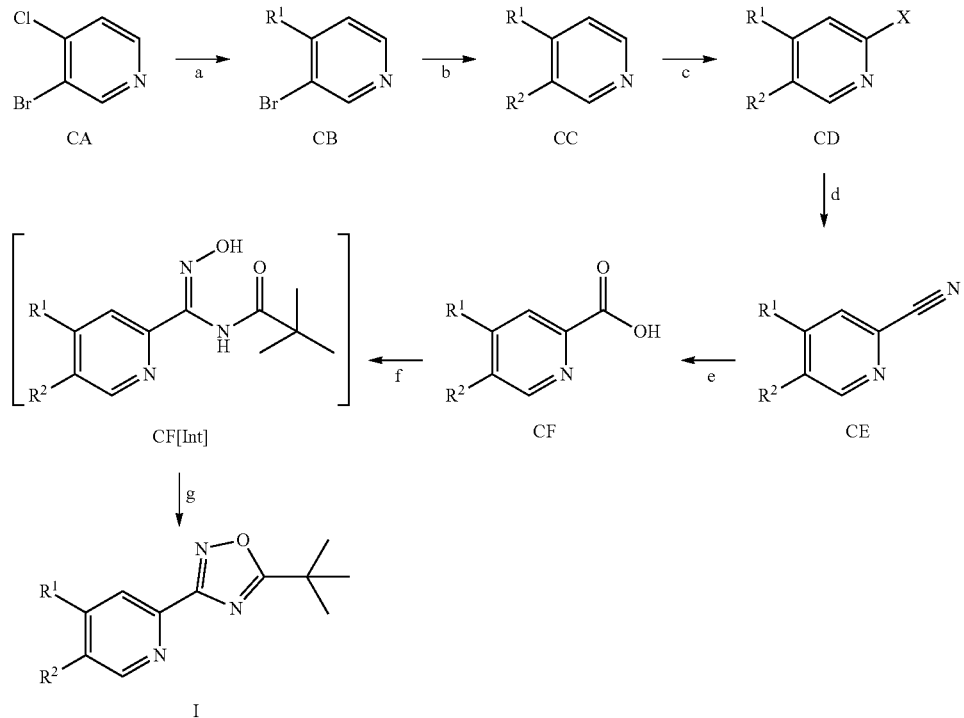

Compound CB can be prepared from CA by reaction with a suitably substituted alcohol as described in the claims, in the presence of a base, for example sodium hydride, with or without an inert solvent, for example dimethylformamide, at temperatures ranging from room temperature to the reflux temperature of the solvent (step a). Optionally, this step can also be carried out at a later point in the synthesis, e.g. after the oxadiazole has been generated as described in step g.

Conversion of compound CB to compound CC can be prepared by coupling a suitably substituted cycloalkyl metal species (e.g. a trifluoroborate [BF$_3$]$^-$K$^+$, a boronic acid B(OH)$_2$ or a boronic acid pinacol ester) (step b), e.g. an organotrifluoroborate potassium salt in the presence of a palladium catalyst such as palladium(II)acetate/butyl-1-adamantylphosphine and a base such as cesium carbonate in an inert solvent such as toluene at temperatures between 50° C. and the boiling temperature of the solvent, or an arylboronic acid or arylboronic acid ester in the presence of a suitable catalyst, in particular a palladium catalyst and more particularly palladium(II)acetate/triphenylphosphine mixtures or palladium(II)chloride-dppf (1,1'-bis(diphenylphosphino)ferrocene) complexes and a base such as triethylamine, sodium carbonate or potassium phosphate in an inert solvent such as dimethylformamide, toluene, tetrahydrofuran, acetonitrile or dimethoxyethane.

CC (X=Cl, Br, I) can be selectively halogenated on position 2 to give CD for example by treatment of N,N-dimethylethanolamine with butyl lithium on CC followed by addition of a source of bromine, e.g. 1,2-dibromotetrachloroethane (step c).

Compound CE can be prepared from CD by addition of cyanide source, e.g. zinc cyanide or copper cyanide in presence of a palladium catalyst such as palladium triphenylphosphine tetrakis or tris(dibenzylideneacetone)dipalladium(0) and dppf, in a solvent such as DMF or dioxane and refluxed to the solvent boiling point temperature (step d).

Hydrolysis of compound CE lead to the picolinic acid CF and can be performed under acidic or basic conditions known to a person skilled in the art, e.g. with aqueous solution of hydrochloric acid at 100° C. (step e).

Cylisation to compound I can be performed by amide coupling methods known to a person skilled in the art, with the suitably substituted commercially available carboxylic acid to give intermediate CF[Int] (step f), followed by heating to cyclise to the oxadiazole ring in a high boiling point solvent such as DMF (step g).

If one of the starting materials, compounds of formulae CA, reagents used in step a, b or f, contains one or more functional groups which are not stable or are reactive under the reaction conditions of one or more reaction steps, appropriate protecting groups (P) (as described e.g. in T. W. Greene et al., Protective Groups in Organic Chemistry, John Wiley and Sons Inc. New York 1999, 3$^{rd}$ edition) can be introduced before the critical step applying methods well known in the art. Such protecting groups can be removed at a later stage of the synthesis using standard methods known in the art.

If one or more compounds of formulae CA to CF contain chiral centers, compounds of formula I can be obtained as mixtures of diastereomers or enantiomers, which can be separated by methods well known in the art, e.g. (chiral) HPLC or crystallization. Racemic compounds can e.g. be separated into their antipodes via diastereomeric salts by crystallization or by separation of the antipodes by specific chromatographic methods using either a chiral adsorbent or a chiral eluent.

The invention also relates to a process for the preparation of a compound of formula (I) comprising
(a) the reaction of a compound of formula (A)

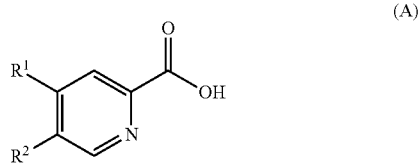

(A)

in the presence of NH$_2$R, an amide bond forming coupling agent and a base; or
(b) heating a compound of formula (B)

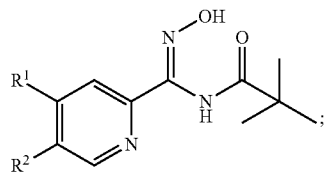

(B)

wherein R is —C(R$^4$R$^5$)$_m$(CH$_2$)$_n$—R$^6$ and wherein R$^1$ to R$^6$ are as defined above.

Examples of amide bond forming coupling agents are N,N'-carbonyl-diimidazole (CDI), N,N'-dicyclohexylcarbodiimide (DCC), 1-(3-dimethylaminopropyl)-3-ethylcarbodiimide hydrochloride (EDCI), 1-[bis(dimethylamino)-methylene]-1H-1,2,3-triazolo[4,5-b]pyridinium-3-oxide hexafluorophosphate (HATU), 1-hydroxy-1,2,3-benzotriazole (HOBT), O-benzotriazol-1-yl-N,N,N',N'-tetramethyl-uronium tetrafluorob orate (TBTU) and O-benzotriazole-N,N,N',N'-tetramethyl-uronium-hexafluorophosphate (HBTU).

Examples of suitable bases are tertiary amine bases like triethylamine, N-methylmorpholine, N,N-diisopropylethylamine or 4-(dimethylamino)-pyridine.

In step (a), the reaction temperature is for example room temperature.

A convenient method for step (a) is to use for example TBTU and a base, for example N-ethyl-N-isopropylpropan-2-amine in an inert solvent such as for example dimethylformamide at room temperature.

In step (b), heating is performed at the boiling point of a high boiling point solvent like e.g. toluene or DMF. Heating can for example be performed at a temperature of above 100° C.

Another embodiment of the invention provides a pharmaceutical composition or medicament containing a compound of the invention and a therapeutically inert carrier, diluent or excipient, as well as a method of using the compounds of the invention to prepare such composition and medicament. In one example, the compound of formula (I) may be formulated by mixing at ambient temperature at the appropriate pH, and at the desired degree of purity, with physiologically acceptable carriers, i.e., carriers that are non-toxic to recipients at the dosages and concentrations employed into a galenical administration form. The pH of the formulation depends mainly on the particular use and the concentration of compound, but preferably ranges anywhere from about 3 to about 8. In one example, a compound of formula (I) is formulated in an acetate buffer, at pH 5. In another embodiment, the compound of formula (I) is sterile. The compound may be stored, for example, as a solid or amorphous composition, as a lyophilized formulation or as an aqueous solution.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may contain components conventional in pharmaceutical preparations, e.g., diluents, carriers, pH modifiers, sweeteners, bulking agents, and further active agents.

A typical formulation is prepared by mixing a compound of the present invention and a carrier or excipient. Suitable carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The invention thus also relates to:

A compound of formula (I) for use as therapeutically active substance;

A pharmaceutical composition comprising a compound of formula (I) and a therapeutically inert carrier;

The use of a compound of formula (I) for the treatment or prophylaxis of pain, neuropathic pain, asthma, osteoporosis, inflammation, psychiatric diseases, psychosis, oncology, encephalitis, malaria, allergy, immunological disorders, arthritis, gastrointestinal disorders, psychiatric disorders rheumatoid arthritis, psychosis or allergy;

The use of a compound of formula (I) for the preparation of a medicament for the treatment or prophylaxis of pain, neuropathic pain, asthma, osteoporosis, inflammation, psychiatric diseases, psychosis, oncology, encephalitis, malaria, allergy, immunological disorders, arthritis, gastrointestinal disorders, psychiatric disorders rheumatoid arthritis, psychosis or allergy;

A compound of formula (I) for use in the treatment or prophylaxis of pain, neuropathic pain, asthma, osteoporosis, inflammation, psychiatric diseases, psychosis, oncology, encephalitis, malaria, allergy, immunological disorders, arthritis, gastrointestinal disorders, psychiatric disorders rheumatoid arthritis, psychosis or allergy; and A method for the treatment or prophylaxis of pain, neuropathic pain, asthma, osteoporosis, inflammation, psychiatric diseases, psychosis, oncology, encephalitis, malaria, allergy, immunological disorders, arthritis, gastrointestinal disorders, psychiatric disorders rheumatoid arthritis, psychosis or allergy, which method comprises administering an effective amount of a compound of formula (I) to a patient in need thereof.

The invention will now be illustrated with the following examples which have no limiting character.

EXAMPLES

Abbreviations

BINAP=2,2'-Bis(diphenylphosphino)-1,1'-binaphthyl; CAN=chemcial abstract service number; DMF=dimethylformamide; DMSO=dimethyl-sulfoxide; EtOAc=ethyl acetate; HATU=2-(3H-[1,2,3]triazolo[4,5-b]pyridin-3-yl)-1,1,3,3-tetramethylisouronium hexafluorophosphate(V); HPLC=LC=high performance liquid chromatography; MS=mass spectrometry; TBTU=O-(benzotriazol-1-yl)-N,N,N',N'-tetramethyl-uronium-tetrafluoroborate; THF=tetrahydrofuran; TLC=thin layer chromatography.

Example 1

5-(Cyclopropylmethoxy)-4-(2,4-dichlorophenyl)-N-[(2S)-1-hydroxy-4-methylpentan-2-yl]pyridine-2-carboxamide

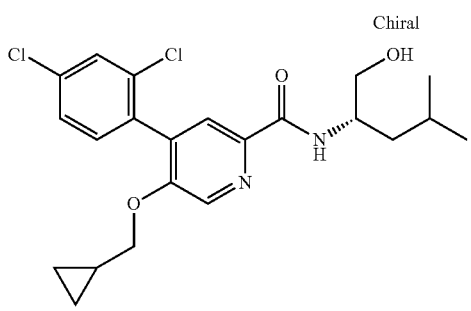 [SMILES: CC(C)C[C@@H](CO)NC(=O)c1cc(-c2ccc(Cl)cc2Cl)c(OCC2CC2)cn1]

a) [6-Chloro-5-(cyclopropylmethoxy)-4-(2,4-dichlorophenyl)-2-pyridyl]methanol

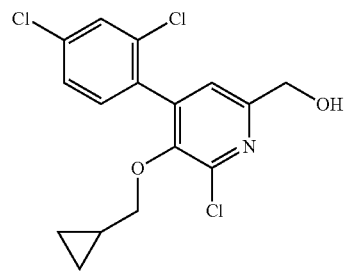 [SMILES: OCc1cc(-c2ccc(Cl)cc2Cl)c(OCC2CC2)c(Cl)n1]

To a suspension of [6-chloro-5-(cyclopropylmethoxy)-4-iodo-2-pyridyl]methanol (1.5 g, 4.4 mmol; CAN 1364677-02-0) in toluene (15 mL) were added [1,1'-dis(diphenylphosphino)ferrocene]dichloropalladium (II) x CH$_2$Cl$_2$ (1:1) (180 mg, 220 µmol), 2,4-dichlorophenylboronic acid (927 mg, 4.9 mmol; CAN 68716-47-2) and a 2 M aqueous solution of Na$_2$CO$_3$ (4.4 mL, 8.8 mmol) under a nitrogen atmosphere. The mixture was stirred at 90° C. for 20 h, cooled to ambient temperature and poured over a chem elut column (Varian, 20 g). The column was washed with EtOAc (50 mL). The solvent was removed under reduced pressure and the residue was purified by column chromatography (silica gel, 70 g, EtOAc/heptane) to obtain the title compound (1.5 g, 95%) as yellow oil, LC-MS: 357.9 [MH$^+$].

b) [5-(Cyclopropylmethoxy)-4-(2,4-dichlorophenyl)-2-pyridyl]methanol

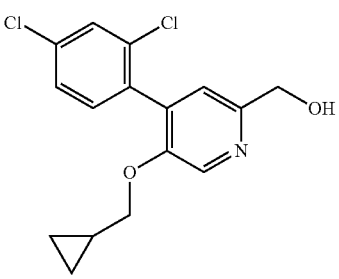 [SMILES: OCc1cc(-c2ccc(Cl)cc2Cl)c(OCC2CC2)cn1]

To a solution of [6-chloro-5-(cyclopropylmethoxy)-4-(2,4-dichlorophenyl)-2-pyridyl]methanol (1.5 g, 4.2 mmol) in 95% acetic acid (4.2 mL) was added tetramethylammonium bromide (6 mg, 42 μmol) under an argon atmosphere. The solution was warmed to 40° C. Within 2 h activated zinc powder (820 mg, 12.5 mmol) was added in five portions. The mixture was stirred for 17 h at 50° C., cooled to ambient temperature, poured onto water (50 mL), and brought to pH 14 by adding 2 N aqueous NaOH solution (30 mL). The mixture was filtered over celite and extracted with EtOAc (200 mL). The layers were separated and the aqueous layer was extracted two more times with EtOAc (2×100 mL). The combined extracts were dried over sodium sulfate, filtered and the filtrate was brought to dryness under reduced pressure. The crude product was purified by column chromatography (silica gel, 90 g, 50% to 100% EtOAc in heptane) to obtain the title compound (800 mg, 59%) as yellow crystals, LC-MS: 324.1 [MH$^+$].

c) 5-(Cyclopropylmethoxy)-4-(2,4-dichlorophenyl)pyridine-2-carboxylic acid

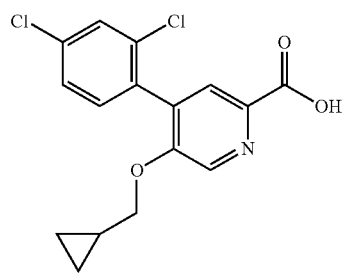 [SMILES: O=C(O)c1cc(-c2ccc(Cl)cc2Cl)c(OCC2CC2)cn1]

To a solution of [5-(cyclopropylmethoxy)-4-(2,4-dichlorophenyl)-2-pyridyl]methanol (780 mg, 2.41 mmol) in pyridine (10 mL) was added a solution of tetrabutylammonium permanganate (2.6 g, 7.22 mmol) in pyridine (10 mL) under an argon atmosphere. The mixture was stirred at 80° C. for 1 h, cooled to ambient temperature and poured onto ice water (250 mL). Saturated aqueous NaHSO$_3$ solution (25 mL) and 2 N aqueous HCl solution (200 mL) were added. The mixture was extracted with diethyl ether (2×250 mL). The combined extracts were dried over sodium sulfate, filtered and the filtrate was evaporated to dryness to obtain the title compound (780 mg, 96%) as light brown solid, LC-MS: 336.1 [M-H$^-$].

d) 5-(Cyclopropylmethoxy)-4-(2,4-dichlorophenyl)-N-[(2S)-1-hydroxy-4-methylpentan-2-yl]pyridine-2-carboxamide To a solution of 5-(cyclopropylmethoxy)-4-(2,4-dichlorophenyl)pyridine-2-carboxylic acid (100 mg, 296 μmol) in DMF (4 mL) were added TBTU (104 mg, 325 μmol), N,N-diisopropyl ethyl amine (191 mg, 253 μL, 1.48 mmol) and L-Leucinol (39 mg, 43 μL, 325 μmol; CAN 7533-40-6). The mixture was shaked for 16 h at ambient temperature at 380 rpm. The solvent was removed in vacuo and the crude purified by column chromatography (silica gel, 20 g, heptane/EtOAc) to obtain the title compound (102 mg, 79%) as colorless foam, LC-MS: 437.1 [MH$^+$].

Example 2

4-(4-Chlorophenyl)-5-(cyclopropylmethoxy)-N-[(1R,2S)-2-hydroxycyclohexyl]pyridine-2-carboxamide

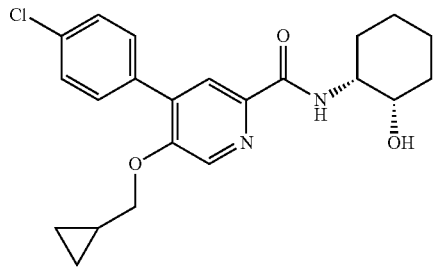 [SMILES: O=C(N[C@@H]1CCCC[C@@H]1O)c1cc(-c2ccc(Cl)cc2)c(OCC2CC2)cn1]

In analogy to the procedure described in example 1 d, 4-(4-chlorophenyl)-5-(cyclopropylmethoxy)pyridine-2-carboxylic acid (200 mg, 658 μmol; CAN 1018782-76-7) was reacted with (1S,2R)-2-amino-cyclohexanol hydrochloride (110 mg, 724 μmol; CAN 200352-28-9) in the presence of TBTU and N,N-diisopropyl ethyl amine to obtain the title compound (236 mg, 89%) as white foam, LC-MS: 401.1628 [MH$^+$].

Example 3

4-(4-Chlorophenyl)-5-(cyclopropylmethoxy)-N-[(1S,2R)-2-hydroxycyclohexyl]pyridine-2-carboxamide

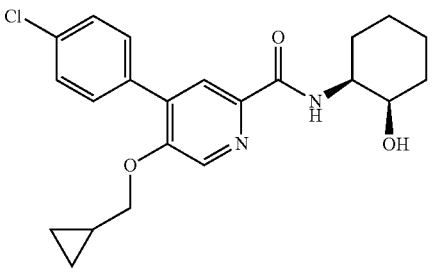 [SMILES: O=C(N[C@H]1CCCC[C@H]1O)c1cc(-c2ccc(Cl)cc2)c(OCC2CC2)cn1]

In analogy to the procedure described in example 1 d, 4-(4-chlorophenyl)-5-(cyclopropylmethoxy)pyridine-2-carboxylic acid (200 mg, 658 μmol; CAN 1018782-76-7) was reacted with (1R,2S)-2-amino-cyclohexanol hydrochloride (110 mg, 724 μmol; CAN 190792-72-4) in the presence of TBTU and N,N-diisopropyl ethyl amine to obtain the title compound (236 mg, 89%) as white solid, LC-MS: 401.1636 [MH$^+$].

Example 4

Methyl 2-[[4-(4-chlorophenyl)-5-(cyclopropylmethoxy)pyridine-2-carbonyl]amino]-2-ethylbutanoate

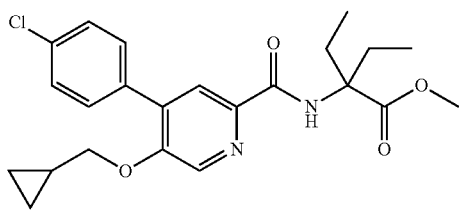 [SMILES: CCC(CC)(NC(=O)c1cc(-c2ccc(Cl)cc2)c(OCC2CC2)cn1)C(=O)OC]

In analogy to the procedure described in example 1 d, 4-(4-chlorophenyl)-5-(cyclopropylmethoxy)pyridine-2-carboxylic acid (200 mg, 658 µmol; CAN 1018782-76-7) was reacted with methyl 2-amino-2-ethyl-butanoate hydrochloride (132 mg, 724 µmol; CAN 92398-54-4) in the presence of TBTU and N,N-diisopropyl ethyl amine to obtain the title compound (264 mg, 93%) as white solid, LC-MS: 431.1742 [MH$^+$].

Example 5

Methyl 2-[[5-(cyclopropylmethoxy)-4-(3,4-dichlorophenyl)pyridine-2-carbonyl]amino]-2-ethylbutanoate

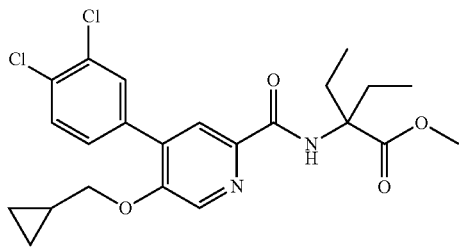 [SMILES: CCC(CC)(NC(=O)c1cc(-c2ccc(Cl)c(Cl)c2)c(OCC2CC2)cn1)C(=O)OC]

a) [6-Chloro-5-(cyclopropylmethoxy)-4-(3,4-dichlorophenyl)-2-pyridyl]methanol

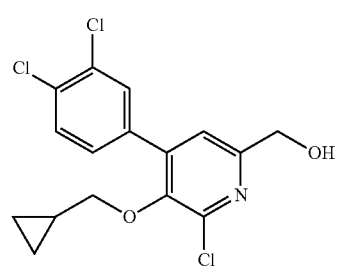 [SMILES: OCc1cc(-c2ccc(Cl)c(Cl)c2)c(OCC2CC2)c(Cl)n1]

In analogy to the procedure described in example 1 a, [6-chloro-5-(cyclopropylmethoxy)-4-iodo-2-pyridyl]methanol (23 g, 68 mmol; CAN 1364677-02-0) was reacted with 3,4-dichlorophenylboronic acid (12.9 g, 68 mmol; CAN 151169-75-4) in the presence of [1,1'-dis(diphenylphosphino)ferrocene]dichloropalladium (II) x CH$_2$Cl$_2$ (1:1) and Na$_2$CO$_3$ to give the title compound (23.6 g, 97%) as off-white solid, LC-MS: 358.0161 [MH$^+$].

b) [5-(Cyclopropylmethoxy)-4-(3,4-dichlorophenyl)-2-pyridyl]methanol

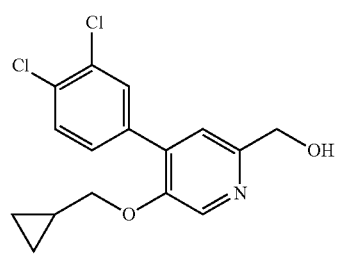 [SMILES: OCc1cc(-c2ccc(Cl)c(Cl)c2)c(OCC2CC2)cn1]

In analogy to the procedure described in example 1 b, [6-chloro-5-(cyclopropylmethoxy)-4-(3,4-dichlorophenyl)-2-pyridyl]methanol (23.6 g, 66 mmol) was reacted with tetramethylammonium bromide and activated zinc powder to obtain the title compound (18.6 g, 87%) as light brown solid, LC-MS: 324.0551 [MH$^+$].

c) 5-(Cyclopropylmethoxy)-4-(3,4-dichlorophenyl)pyridine-2-carboxylic acid

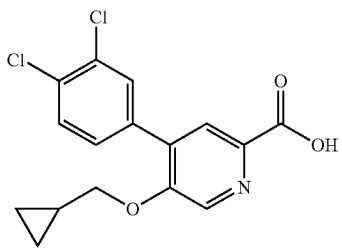 [SMILES: O=C(O)c1cc(-c2ccc(Cl)c(Cl)c2)c(OCC2CC2)cn1]

In analogy to the procedure described in example 1 c, [5-(cyclopropylmethoxy)-4-(3,4-dichlorophenyl)-2-pyridyl]methanol (18.6 g, 57 mmol) was oxidized with tetrabutylammonium permanganate in pyridine to give the title compound (19.1 g, 98%) as off-white solid, LC-MS: 336.1 [M-H$^-$].

d) Methyl 2-[[5-(cyclopropylmethoxy)-4-(3,4-dichlorophenyl)pyridine-2-carbonyl]amino]-2-ethylbutanoate In analogy to the procedure described in example 1 d, 5-(cyclopropylmethoxy)-4-(3,4-dichlorophenyl)pyridine-2-carboxylic acid (200 mg, 591 µmol) was reacted with methyl 2-amino-2-ethyl-butanoate hydrochloride (118 mg, 651 µmol; CAN 92398-54-4) in the presence of TBTU and N,N-diisopropyl ethyl amine to obtain the title compound (238 mg, 86%) as white solid, LC-MS: 465.1333 [MH$^+$].

Example 6

Methyl 2-[[5-(cyclopropylmethoxy)-4-(3,4-dichlorophenyl)pyridine-2-carbonyl]amino]-2-ethylbutanoate

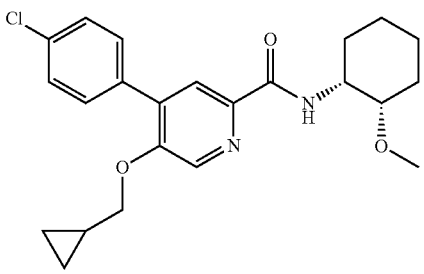 [SMILES: CO[C@H]1CCCC[C@H]1NC(=O)c1cc(-c2ccc(Cl)cc2)c(OCC2CC2)cn1]

To an ice cold solution of 4-(4-chlorophenyl)-5-(cyclopropylmethoxy)-N-[(1R,2S)-2-hydroxycyclohexyl]pyridine-2-carboxamide (70 mg, 175 µmol; example 2) in THF (5 mL) was added a 60% dispersion of sodium hydride in mineral oil (8.4 mg, 210 µmol). The mixture was stirred for 1 h at ambient temperature. Methyl iodide (24.8 mg, 10.9 µL, 175 µmol) was added and stirring was continued for 23 h. The suspension was poured onto ice water and extracted with EtOAc (2×60 mL). The combined extracts were dried over sodium sulfate, filtered and the filtrate was brought to dryness. The crude product was purified by column chromatography (silica gel, 10 g, EtOAc/heptane) to obtain the title compound (28 mg, 39%) as colorless oil, LC-MS: 415.1784 [MH$^+$].

Example 7

5-Chloro-4-(cyclopropylmethoxy)-N-[(1R)-2-hydroxy-1-phenylethyl]pyridine-2-carboxamide

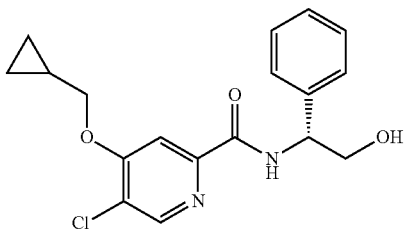 [SMILES: O=C(N[C@@H](CO)c1ccccc1)c1cc(OCC2CC2)c(Cl)cn1]

In analogy to the procedure described in example 1 d, 5-chloro-4-(cyclopropylmethoxy)pyridine-2-carboxylic acid (68 mg, 300 µmol; CAN 1613238-32-6) was reacted with (2R)-2-amino-2-phenyl-ethanol (49 mg, 360 µmol; CAN 56613-80-0) in the presence of TBTU and N,N-diisopropyl ethyl amine to obtain the title compound (54 mg, 52%) as colorless oil, LC-MS: 347.1161 [MH$^+$].

Example 8

5-Chloro-4-(cyclopropylmethoxy)-N-[(2S)-3,3-dimethyl-1-(methylamino)-1-oxobutan-2-yl]pyridine-2-carboxamide

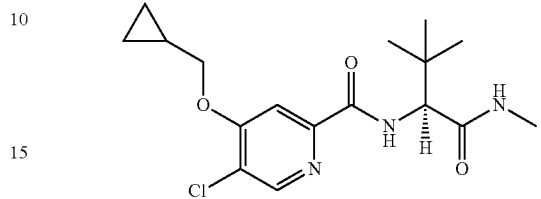

In analogy to the procedure described in example 1 d, 5-chloro-4-(cyclopropylmethoxy)pyridine-2-carboxylic acid (68 mg, 300 µmol; CAN 1613238-32-6) was reacted with (2S)-2-amino-N,3,3-trimethyl-butanamide (51 mg, 360 µmol; CAN 89226-12-0) in the presence of HATU (137 mg, 360 µmol) and N,N-diisopropyl ethyl amine to obtain the title compound (91 mg, 86%) as colorless oil, LC-MS: 354.1581 [MH$^+$].

Example 9

(−) 5-Chloro-4-(cyclopropylmethoxy)-N-[2,2,2-trifluoro-1-pyridin-2-ylethyl]pyridine-2-carboxamide

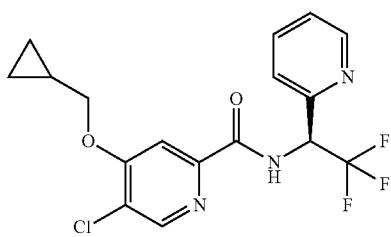 [SMILES: O=C(N[C@@H](c1ccccn1)C(F)(F)F)c1cc(OCC2CC2)c(Cl)cn1]

In analogy to the procedure described in example 1 d, 5-chloro-4-(cyclopropylmethoxy)pyridine-2-carboxylic acid (68 mg, 300 µmol; CAN 1613238-32-6) was reacted with 2,2,2-trifluoro-1-(2-pyridyl)ethanamine (62 mg, 350 µmol; CAN 503173-14-6) in the presence of HATU (137 mg, 360 µmol) and N,N-diisopropyl ethyl amine to obtain (rac) 5-chloro-4-(cyclopropylmethoxy)-N-[2,2,2-trifluoro-1-pyridin-2-ylethyl]pyridine-2-carboxamide which was purified by chiral preparative HPLC to provide the title compound (37 mg, 32%) as colorless oil, LC-MS: 386.0878 [MH$^+$].

Example 10

5-Chloro-4-(cyclopropylmethoxy)-N-[(1R)-2,2,2-trifluoro-1-pyridin-3-ylethyl]pyridine-2-carboxamide

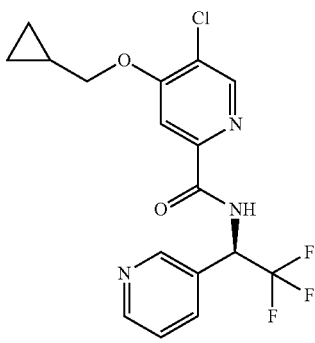 [SMILES: O=C(N[C@H](c1cccnc1)C(F)(F)F)c1cc(OCC2CC2)c(Cl)cn1]

In analogy to the procedure described in example 1 d, 5-chloro-4-(cyclopropylmethoxy)pyridine-2-carboxylic acid (23 mg, 100 µmol; CAN 1613238-32-6) was reacted with (1R)-2,2,2-trifluoro-1-(3-pyridyl)ethanamine; CAN 1212813-98-3) in the presence of HATU (137 mg, 360 µmol) and N,N-diisopropyl ethyl amine to obtain the title compound (30 mg, 78%) as colorless oil, LC-MS: 386.0878 [MH$^+$].

Example 11

5-Chloro-4-(cyclopropylmethoxy)-N-[(2S)-4-methyl-1-(methylamino)-1-oxopentan-2-yl]pyridine-2-carboxamide

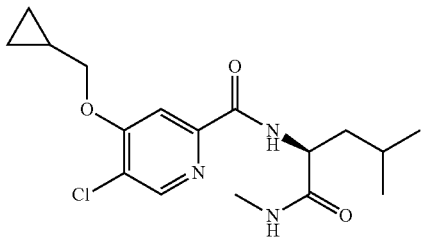 [SMILES: CNC(=O)[C@H](CC(C)C)NC(=O)c1cc(OCC2CC2)c(Cl)cn1]

In analogy to the procedure described in example 1 d, 5-chloro-4-(cyclopropylmethoxy)pyridine-2-carboxylic acid (20 mg, 88 µmol; CAN 1613238-32-6) was reacted with (S)-2-amino-N,4-dimethylpentanamide*HCl (21 mg, 114 µmol; CAN 99145-71-8) in the presence of HATU (137 mg, 360 µmol) and N,N-diisopropyl ethyl amine to obtain the title compound (31 mg, quant.) as light yellow oil, LC-MS: 354.1578 [MH$^+$].

Example 12

5-Chloro-4-(cyclopropylmethoxy)-N-[(2R)-4-methyl-1-(methylamino)-1-oxopentan-2-yl]pyridine-2-carboxamide

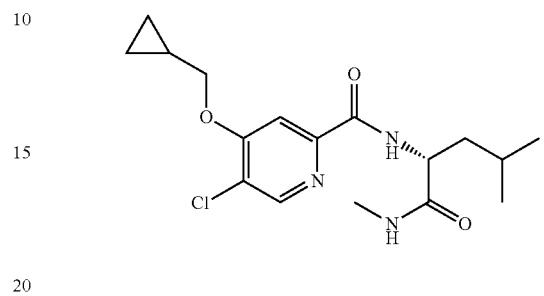

In analogy to the procedure described in example 1 d, 5-chloro-4-(cyclopropylmethoxy)pyridine-2-carboxylic acid (20 mg, 88 µmol; CAN 1613238-32-6) was reacted with (R)-2-amino-N,4-dimethylpentanamide*HCl (21 mg, 114 µmol; CAN 99145-71-8) in the presence of HATU (137 mg, 360 µmol) and N,N-diisopropyl ethyl amine to obtain the title compound (31 mg, quant.) as light yellow oil, LC-MS: 354.1573 [MH$^+$].

Example 13

5-Cyclopropyl-N-[(2S)-3,3-dimethyl-1-(methylamino)-1-oxobutan-2-yl]-4-[(3-methyloxetan-3-yl)methoxy]pyridine-2-carboxamide

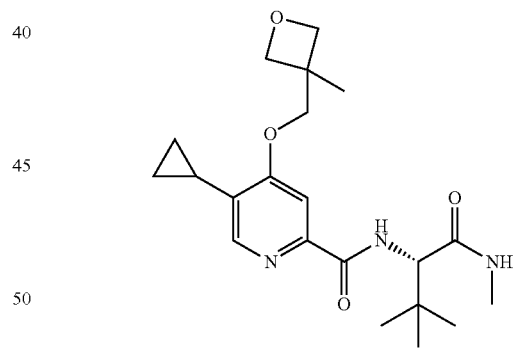

To a solution of 5-cyclopropyl-4-[(3-methyloxetan-3-yl)methoxy]pyridine-2-carboxylic acid (39 mg, 150 µmol; CAN 1613239-78-3) in dry DMF (1.5 mL) was added 4-(4,6-dimethoxy-1,3,5-triazin-2-yl)-4-methylmorpholinium chloride (46 mg, 165 µmol) and N,N-diisopropyl ethyl amine (68 mg, 92 µL, 525 µmol). The reaction mixture was stirred at ambient temperature for 45 min followed by the addition of (2S)-2-amino-N,3,3-trimethyl-butanamide (24 mg, 165 µmol; CAN 89226-12-0). Stirring was continued for 14 h and the crude mixture was purified by preparative HPLC to obtain the title compound, LC-MS: 390.4 [MH$^+$].

Example 14

6-[6-(5-tert-Butyl-1,2,4-oxadiazol-3-yl)-4-(cyclopropylmethoxy)pyridin-3-yl]-2-oxa-6-azaspiro[3.3]heptane

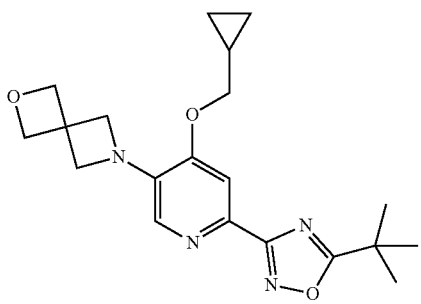 [SMILES: CC(C)(C)c1nc(-c2cc(OCC3CC3)c(N3CC4(COC4)C3)cn2)no1]

To a solution of 3-(5-bromo-4-(cyclopropylmethoxy)pyridin-2-yl)-5-tert-butyl-1,2,4-oxadiazole (60 mg, 170 µmol; CAN 1629991-68-9) in dry toluene (1 mL) under an argon atmosphere were added 2-oxa-6-azaspiro[3.3]heptane hemioxalate (29.5 mg, 102 µmol; CAN 1045709-32-7), Pd(OAc)$_2$ (3.8 mg, 17 µmol), BINAP (10.6 mg, 17 µmol) and Cs$_2$CO$_3$ (111 mg, 341 µmol). The reaction mixture was stirred at 115° C. for 14 h, filtered over a pad of Celite and the filtrate was evaporated to dryness. The crude product was purified by column chromatography (silica gel, 10 g, EtOAc/heptane) to obtain the title compound (15 mg, 24%), LC-MS: 371.0 [MH$^+$].

Example 15 tert-Butyl (2S)-2-[[2-(5-tert-butyl-1,2,4-oxadiazol-3-yl)-5-cyclopropylpyridin-4-yl]oxymethyl]pyrrolidine-1-carboxylate

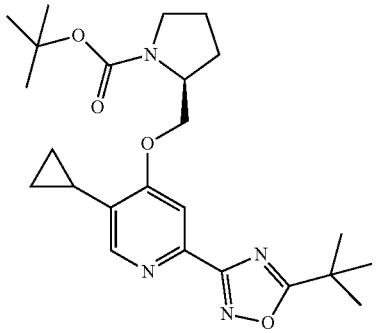 [SMILES: CC(C)(C)OC(=O)N1CCC[C@H]1COc1cc(-c2noc(C(C)(C)C)n2)ncc1C1CC1]

To a solution of 5-tert-butyl-3-(4-chloro-5-cyclopropylpyridin-2-yl)-1,2,4-oxadiazole (50 mg, 180 µmol; CAN 1629991-73-6) in dry DMF (1 mL) were added NaH (10.8 mg, 270 mol) and Boc-L-prolinol (54.3 mg, 270 µmol; CAN 69610-40-8). The reaction mixture was stirred at ambient temperature for 15 min and subsequently under microwave irradiation for 30 min at 100° C. Quenching with ice water and purification via preparative HPLC provided the title compound (6 mg, 7%), LC-MS: 443.7 [MH$^+$].

Example 16 tert-Butyl (3R)-3-[2-(5-tert-butyl-1,2,4-oxadiazol-3-yl)-5-cyclopropylpyridin-4-yl]oxypyrrolidine-1-carboxylate

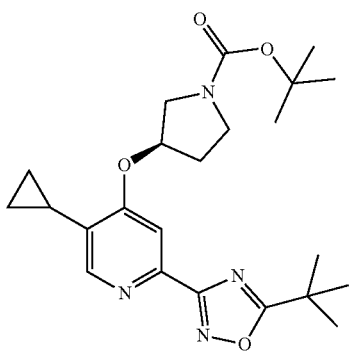 [SMILES: CC(C)(C)OC(=O)N1CC[C@@H](Oc2cc(-c3noc(C(C)(C)C)n3)ncc2C2CC2)C1]

In analogy to the procedure described in example 15, 5-tert-butyl-3-(4-chloro-5-cyclopropylpyridin-2-yl)-1,2,4-oxadiazole (50 mg, 180 µmol; CAN 1629991-73-6) was reacted with Boc-(R)-3-hydroxypyrrolidine (50.6 mg, 270 µmol; CAN 109431-87-0) in the presence of NaH to obtain the title compound (43 mg, 56%), LC-MS: 429.7 [MH$^+$].

Example 17

5-tert-Butyl-3-[5-cyclopropyl-4-[(3-methylsulfonylphenyl)methoxy]pyridin-2-yl]-1,2,4-oxadiazole

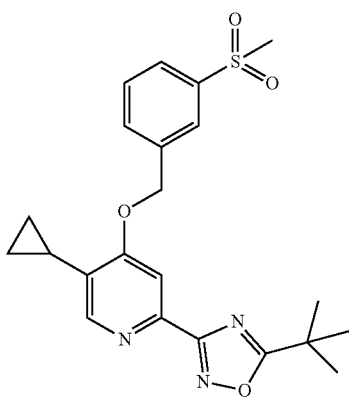 [SMILES: CC(C)(C)c1nc(-c2cc(OCc3cccc(S(C)(=O)=O)c3)c(C3CC3)cn2)no1]

In analogy to the procedure described in example 15, 5-tert-butyl-3-(4-chloro-5-cyclopropylpyridin-2-yl)-1,2,4-oxadiazole (50 mg, 180 µmol; CAN 1629991-73-6) was reacted with (3-(methylsulfonyl)phenyl)methanol (30 mg, 161 µmol; CAN 220798-39-0) in the presence of NaH to obtain the title compound (8 mg, 10%), LC-MS: 428.6 [MH$^+$].

Example 18

N-[1-(azetidin-3-yl)-1-(5-methyl-1,3,4-oxadiazol-2-yl)ethyl]-5-cyclopropyl-4-(2,2,2-trifluoroethoxy)pyridine-2-carboxamide

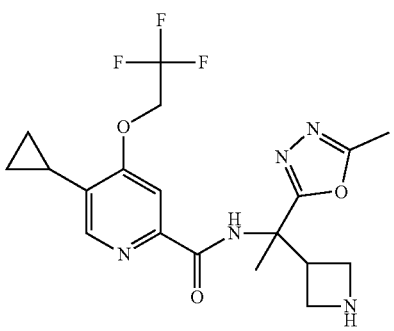 [SMILES: Cc1nnc(C(C)(NC(=O)c2cc(OCC(F)(F)F)c(C3CC3)cn2)C2CNC2)o1]

a) 1-(1-Benzhydrylazetidin-3-yl)ethanone

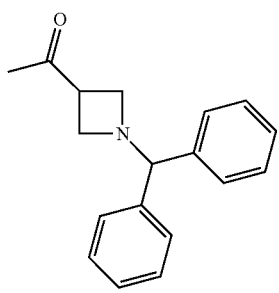 [SMILES: CC(=O)C1CN(C(c2ccccc2)c2ccccc2)C1]

To a solution of 1-benzhydryl-N-methoxy-N-methylazetidine-3-carboxamide (1.62 g, 5.22 mmol, CAN 359402-66-7) in dry THF (30 mL) cooled to −78° C. under an argon atmosphere was slowly added a 1.6 M solution of methyl lithium in diethyl ether (3.75 mL, 6 mmol). The reaction mixture was stirred at −78° C. for 30 min and for 14 h at ambient temperature. After cooling to −15° C. a 1.6 M solution of methyl lithium in diethyl ether (1.63 mL, 2.61 mmol) was added. The reaction mixture was stirred at −15° C. for 1 h, water was carefully added and stirring was continued at 0° C. for 10 min. The reaction medium was diluted with ethyl acetate and washed with 1 M aq. NaHCO₃ solution. The layers were separated, the aqueous layer was extracted with ethy acetate and the combined organic phases were dried over Na₂SO₄. After filtration the solvent was removed under reduced pressure. The residue was purified by column chromatography (silica gel, 50 g, ethyl acetate/heptane) to obtain the title compound (1.1 g, 80%), LC-MS: 266.5 [MH⁺].

b) (E)-N-(1-(1-Benzhydrylazetidin-3-yl)ethylidene)-2-methylpropane-2-sulfinamide

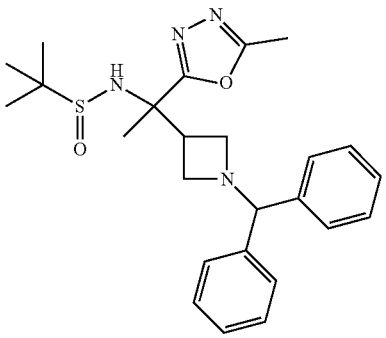 [SMILES: Cc1nnc(C(C)(NS(=O)C(C)(C)C)C2CN(C(c3ccccc3)c3ccccc3)C2)o1]

To a solution of 1-(1-benzhydrylazetidin-3-yl)ethanone (1.1 g, 4.15 mmol) in dry THF (30 mL) under an argon atmosphere were added 2-methylpropane-2-sulfinamide (528 mg, 4.35 mmol; CAN 146374-27-8) and titanium(IV) ethoxide (993 mg, 913 µL, 4.35 mmol). The reaction mixture was stirred at 70° C. for 16 h and carefully quenched by addition of saturated aqueous NaCl solution (5 mL). Stirring was continued at ambient temperature for 20 min. The formed precipitate was removed by filtration over a pad of Celite. The filter cake was washed twice with THF. The filtrate was brought to dryness, redissolved in ethyl acetate and washed with brine. After drying over Na₂SO₄ and filtration the solvent was removed under reduced pressure. The residue was purified by column chromatography (silica gel, 70 g, ethyl acetate/heptane) to obtain the title compound (975 mg, 64%), LC-MS: 369.6 [MH⁺].

c) N-(1-(1-Benzhydrylazetidin-3-yl)-1-(5-methyl-1,3,4-oxadiazol-2-yl)ethyl)-2-methylpropane-2-sulfinamide To a solution of 2-bromo-5-methyl-1,3,4-oxadiazole (243 mg, 1.49 mmol; CAN 864750-58-3) in dry THF (5 mL) cooled to −15° C. under an argon atmosphere was added a 1.3 M isopropyl magnesium chloride lithium chloride complex solution in THF (1.15 mL, 1.49 mmol). The reaction mixture was stirred at −15° C. for 30 min followed by addition of a mixture of a 2 M trimethylaluminum solution in heptane (746 µL, 1.49 mmol) and (E)-N-(1-(1-benzhydrylazetidin-3-yl)ethylidene)-2-methylpropane-2-sulfinamide (0.5 g, 1.36 mmol) in dry toluene (8 mL). The mixture was stirred at ambient temperature for 14 h and carefully quenched by dropwise addition of water. Ethyl acetate and 1 M aq. NaHCO₃ solution were added. The layers were separated. The aqueous layer was extracted with ethyl acetate. The combined organic layers were dried over Na₂SO₄, filtered and the filtrate was brought to dryness. The residue was purified by column chromatography (silica gel, 70 g, dichloromethane/methanol) to obtain the title compound (443 mg, 72%), LC-MS: 453.6 [MH⁺].

d) 1-(1-Benzhydrylazetidin-3-yl)-1-(5-methyl-1,3,4-oxadiazol-2-yl)ethanamine

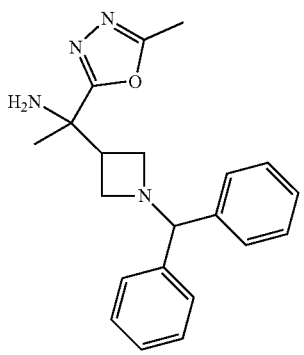 [SMILES: Cc1nnc(C(C)(N)C2CN(C(c3ccccc3)c3ccccc3)C2)o1]

To a solution of N-(1-(1-benzhydrylazetidin-3-yl)-1-(5-methyl-1,3,4-oxadiazol-2-yl)ethyl)-2-methylpropane-2-sulfinamide (433 mg, 957 μmol) in MeOH (5 mL) was added a 4 M solution of HCl in dioxane (598 μL, 2.39 mmol). The reaction mixture was stirred for 2 h at ambient temperature and concentrated in vacuo. The residue was redissolved in ethyl acetate and washed with 2 M aq. Na₂CO₃ solution. The aqueous layer was extracted with ethyl acetate. The combined organic layers were dried over Na₂SO₄, filtered and the filtrate was brought to dryness. The residue was purified by column chromatography (silica gel, 20 g, dichloromethane/methanol) to obtain the title compound (123 mg, 37%), LC-MS: 349.6 [MH⁺].

e) N-(1-(1-Benzhydrylazetidin-3-yl)-1-(5-methyl-1,3,4-oxadiazol-2-yl)ethyl)-5-cyclopropyl-4-(2,2,2-trifluoroethoxy)picolinamide

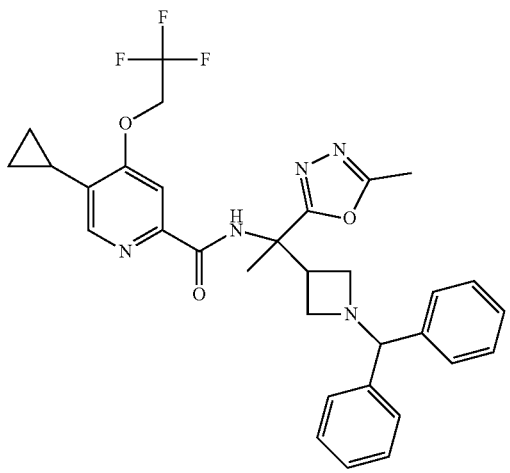 [SMILES: Cc1nnc(C(C)(NC(=O)c2cc(OCC(F)(F)F)c(C3CC3)cn2)C2CN(C(c3ccccc3)c3ccccc3)C2)o1]

In analogy to the procedure described in example 1 d, 5-cyclopropyl-4-(2,2,2-trifluoroethoxy)picolinic acid (85 mg, 325 μmol; CAN 1613238-51-9) was reacted with 1-(1-benzhydrylazetidin-3-yl)-1-(5-methyl-1,3,4-oxadiazol-2-yl)ethanamine (119 mg, 342 mol) in the presence of TBTU and N,N-diisopropyl ethyl amine to obtain the title compound (100 mg, 52%), LC-MS: 592.6 [MH⁺].

f) N-[1-(Azetidin-3-yl)-1-(5-methyl-1,3,4-oxadiazol-2-yl)ethyl]-5-cyclopropyl-4-(2,2,2-trifluoroethoxy)pyridine-2-carboxamide To a solution of N-(1-(1-benzhydrylazetidin-3-yl)-1-(5-methyl-1,3,4-oxadiazol-2-yl)ethyl)-5-cyclopropyl-4-(2,2,2-trifluoroethoxy)picolinamide (100 mg, 169 μmol) in EtOH (1 mL) under an argon atmosphere were added a 4 M aqueous HCl solution (30.8 mg, 25.7 μL, 845 μmol) and Pd/C 10% (10% w/w, 10 mg, 94 μmol). The reaction was put under an H₂ atmosphere of 2.5 bar and stirred at room temperature for 14 h. Trifluoro acetic acid (193 mg, 130 μL, 1.69 mmol) and Pd/C 10% (10% w/w, 10 mg, 94 μmol) were added to the mixture. Stirring was continued at 50° C. under an H₂ atmosphere of 2 bar for 3 h. The mixture was filtered through a pad of Celite and the filter cake was washed twice with ethanol. The filtrate was concentrated and the crude was immediately purified by preparative HPLC to obtain the title compound (25 mg, 35%) as white solid, LC-MS: 426.3 [MH⁺].

Example 19

Ethyl 2-[[5-cyclopropyl-4-[(3-methyloxetan-3-yl)methoxy]pyridine-2-carbonyl]amino]-2-ethylbutanoate

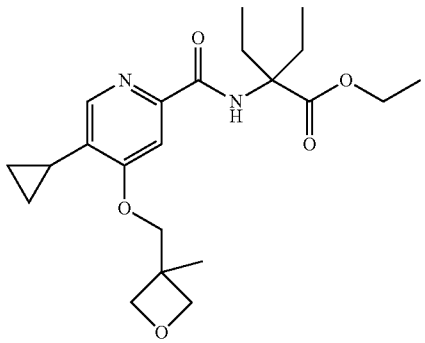 [SMILES: CCOC(=O)C(CC)(CC)NC(=O)c1cc(OCC2(C)COC2)c(C2CC2)cn1]

In analogy to the procedure described in example 13, 5-cyclopropyl-4-((3-methyloxetan-3-yl)methoxy)picolinic acid (19.5 mg, 74.1 μmol; CAN 1613239-78-3) was reacted with ethyl 2-amino-2-ethylbutanoate hydrochloride (14.5 mg, 74 μmol; CAN 1135219-29-2) in the presence of 4-(4,6-dimethoxy-1,3,5-triazin-2-yl)-4-methylmorpholin-4-ium chloride and N,N-diisopropyl ethyl amine to give the title compound (26 mg, 86%), LC-MS: 405.7 [MH⁺].

Example 20

5-Chloro-N-[1-cyclopropyl-2-(5-methyl-1,2,4-oxadiazol-3-yl)propan-2-yl]-4-[(2,2-difluoro-1-methylcyclopropyl)methoxy]pyridine-2-carboxamide

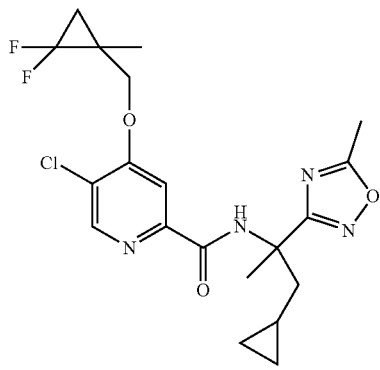 [SMILES: Cc1nc(C(C)(CC2CC2)NC(=O)c2cc(OCC3(C)CC3(F)F)c(Cl)cn2)no1]

a) 4,5-Dichloro-N-(1-cyclopropyl-2-(5-methyl-1,2,4-oxadiazol-3-yl)propan-2-yl)picolinamide

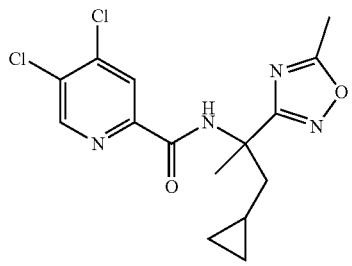 [SMILES: Cc1nc(C(C)(CC2CC2)NC(=O)c2cc(Cl)c(Cl)cn2)no1]

A mixture of 4,5-dichloropicolinic acid (100 mg, 521 µmol; CAN 73455-13-7), 1-cyclopropyl-2-(5-methyl-1,2,4-oxadiazol-3-yl)propan-2-amine hydrochloride (136 mg, 625 mol; CAN 1415900-39-8), 2-bromo-1-ethylpyridinium tetrafluoroborate (284 mg, 885 mol) and N,N-diisopropyl ethyl amine (212 mg, 281 µL) in dioxane (0.8 mL) was stirred for 14 h at 80° C., poured onto ice/brine (1×25 mL) and extracted with EtOAc (2×25 mL). The combined extracts were washed with ice water/brine (25 mL), dried over $Na_2SO_4$ and filtered. The filtrate was brought to dryness and the residue was purified by column chromatography (silica gel, 10 g, heptane/ethyl acetate) to obtain the title compound (120 mg, 65%) as colorless liquid, LC-MS: 355.2 [MH⁺].

b) 5-Chloro-N-[1-cyclopropyl-2-(5-methyl-1,2,4-oxadiazol-3-yl)propan-2-yl]-4-[(2,2-difluoro-1-methylcyclopropyl)methoxy]pyridine-2-carboxamide Potassium tert-butoxyde (28 mg, 246 µmol) and potassium benzoate (39.4 mg, 246 µmol) were added to a solution of (2,2-difluoro-1-methylcyclopropyl)methanol (15 mg, 123 mol; CAN 128230-72-8) and 4,5-dichloro-N-(1-cyclopropyl-2-(5-methyl-1,2,4-oxadiazol-3-yl)propan-2-yl)picolinamide (65.5 mg, 184 µmol) in DMF (375 µL). The mixture was heated for 5 h at 130° C. in a microwave oven, poured onto ice/0.1N HCl (1×25 mL) and extracted with EtOAc (2×50 mL). The combined extracts were washed with ice/brine (1×25 mL), dried over $Na_2SO_4$ and brought to dryness after filtering. The crude was purified by preparative TLC (silica gel, 1.0 mm, hexanes/EtOAc 1:1) to give the title compound, LC-MS: 441.2 [MH⁺].

Example 21

4-(Benzotriazol-1-yloxy)-N-[1-cyclopropyl-2-(5-methyl-1,2,4-oxadiazol-3-yl)propan-2-yl]-5-(trifluoromethyl)pyridine-2-carboxamide

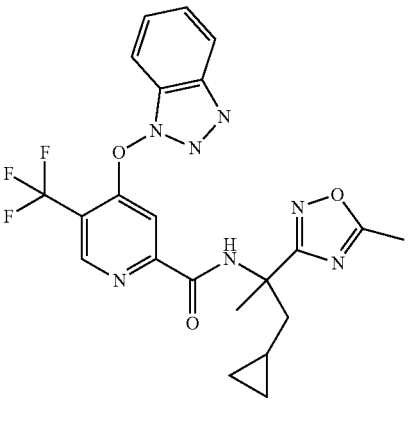 [SMILES: Cc1nc(C(C)(CC2CC2)NC(=O)c2cc(ON3NNc4ccccc43)c(C(F)(F)F)cn2)no1]

A mixture of 4-chloro-5-(trifluoromethyl)picolinic acid (20 mg, 88.7 µmol; CAN 1211591-26-2) 1-cyclopropyl-2-(5-methyl-1,2,4-oxadiazol-3-yl)propan-2-amine hydrochloride (23.2 mg, 106 µmol; CAN 1415900-39-8), TBTU (48.4 mg, 151 µmol) and N,N-diisopropyl ethyl amine (36.1 mg, 47.8 µL, 279 µmol) in DMF (200 µL) was stirred at ambient temperature for 3 h, poured onto ice/brine/1N HCl (25 mL) and extracted with EtOAc (2×25 mL). The combined extracts were washed with saturated aqueous $NaHCO_3$-solution (25 mL) and ice water/brine (25 mL), dried over $Na_2SO_4$ and filtered. The filtrate was brought to dryness and the residue was purified by preparative TLC (silica gel, 2.0 mm, hexanes/EtOAc 1:1) to obtain the title compound (27 mg, 63%) as colorless liquid, LC-MS: 488.2 [MH⁺].

Example 22

N-(4-Amino-2-cyclopropyl-4-oxobutan-2-yl)-5-cyclopropyl-4-[(5-fluoropyridin-2-yl)methoxy]pyridine-2-carboxamide

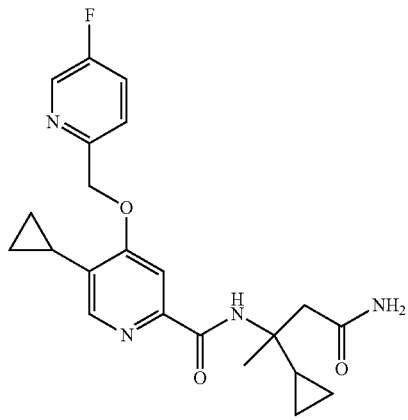 [SMILES: CC(CC(N)=O)(NC(=O)c1cc(OCc2ccc(F)cn2)c(C2CC2)cn1)C1CC1]

a) N-(4-amino-2-cyclopropyl-4-oxobutan-2-yl)-4-chloro-5-cyclopropylpicolinamide

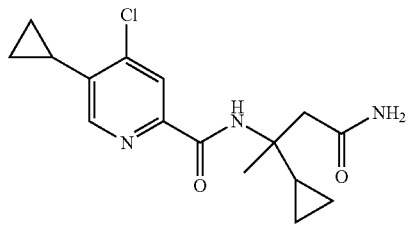 [SMILES: CC(CC(N)=O)(NC(=O)c1cc(Cl)c(C2CC2)cn1)C1CC1]

In analogy to the procedure described in example 20 a, 4-chloro-5-cyclopropylpicolinic acid (80 mg, 405 µmol; CAN 1256790-74-5) was reacted with 3-amino-3-cyclopropylbutanamide hydrochloride (145 mg, 486 µmol; CAN of free base: 1534510-01-4) in the presence of 2-bromo-1-ethylpyridinium tetrafluoroborate and N,N-diisopropyl ethyl amine to obtain the title compound (55 mg, 42%) as colorless liquid, LC-MS: 322.2 [MH$^+$].

b) N-(4-Amino-2-cyclopropyl-4-oxobutan-2-yl)-5-cyclopropyl-4-[(5-fluoropyridin-2-yl)methoxy]pyridine-2-carboxamide Potassium tert-butoxyde (13.9 mg, 124 µmol) and potassium benzoate (19.9 mg, 124 mol) were added to a solution of N-(4-amino-2-cyclopropyl-4-oxobutan-2-yl)-4-chloro-5-cyclopropylpicolinamide (20 mg, 62.2 µmol) and (5-fluoropyridin-2-yl)methanol (9.48 mg, 74.6 µmol; CAN 802325-29-7) in DMF (500 µL). The reaction mixture was heated for 5 h to 130° C. in a microwave oven, poured onto ice/0.1N HCl (25 mL) and extracted with EtOAc (2×50 mL). The combined extracts were washed with ice/brine (25 mL), dried over Na$_2$SO$_4$ and filtered. The filtrate was brought to dryness and the residue was purified by preparative TLC (silica gel, 2.0 mm, EtOAc) to obtain the title compound (2 mg, 8%) as colorless liquid, LC-MS: 413.2 [MH$^+$].

Example 23

N-[(2S)-1-Cyclopropyl-2-(5-methyl-1,2,4-oxadiazol-3-yl)propan-2-yl]-4-(6-fluoropyridin-3-yl)-5-phenylmethoxypyridine-2-carboxamide

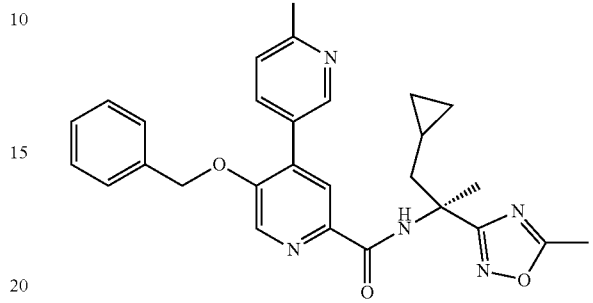

a) Methyl 5-(benzyloxy)-4-bromopicolinate

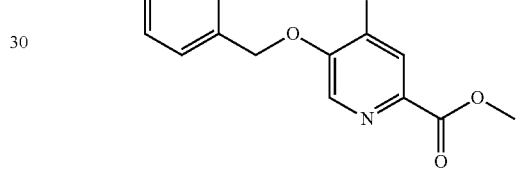

A mixture of methyl 4-bromo-5-hydroxypicolinate (200 mg, 862 µmol; CAN 1256836-99-3), potassium carbonate (477 mg, 3.45 mmol) and (chloromethyl)benzene (164 mg, 149 µL, 1.29 mmol; CAN 100-44-7) in DMF (8 mL) was stirred for 20 h at ambient temperature. Stirring was continued at 50° C. for 8 h, then the reaction mixture was poured onto ice water/brine (25 mL) and extracted with EtOAc (2×50 mL). The combined extracts were washed with ice water/brine (2×25 mL), dried over Na$_2$SO$_4$ and filtered. The filtrate was brought to dryness and the residue was purified by preparative column chromatography (silica gel, 10 g, heptanes/EtOAc) to obtain the title compound (155 mg, 56%) as off-white solid, LC-MS: 324.1 [MH$^+$].

b) 5-(Benzyloxy)-4-bromopicolinic acid

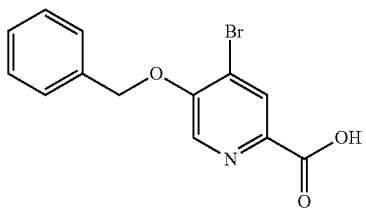 [SMILES: O=C(O)c1cc(Br)c(OCc2ccccc2)cn1]

A mixture of methyl 5-(benzyloxy)-4-bromopicolinate (153 mg, 475 µmol) and lithium hydroxide hydrate (29.9 mg, 712 µmol) in THF (1.5 mL) and water (0.75 mL) was stirred at ambient temperature for 20 h, poured onto ice water/0.1N aqueous HCl solution (25 mL) and extracted with EtOAc (2×25 mL). The combined extracts were washed ice water/brine (25 mL), dried over Na$_2$SO$_4$ and filtered. The filtrate was brought to dryness to obtain the title compound (128 mg, 88%) as off-white solid, LC-MS: 308.1 [MH$^+$].

c) (S)-5-(Benzyloxy)-4-bromo-N-(1-cyclopropyl-2-(5-methyl-1,2,4-oxadiazol-3-yl)propan-2-yl)picolinamide

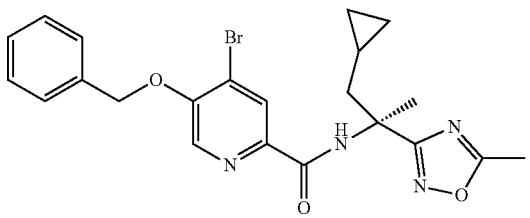 [SMILES: Cc1nc([C@](C)(CC2CC2)NC(=O)c2cc(Br)c(OCc3ccccc3)cn2)no1]

In analogy to the procedure described in example 20 a, 5-(benzyloxy)-4-bromopicolinic acid (30 mg, 97.4 µmol) was reacted with (S)-1-cyclopropyl-2-(5-methyl-1,2,4-oxadiazol-3-yl)propan-2-amine hydrochloride (25.4 mg, 117 µmol; (S)-enantiomer of CAN 1415900-39-8) in the presence of 2-bromo-1-ethylpyridinium tetrafluoroborate and N,N-diisopropyl ethyl amine to obtain the title compound (38 mg, 42%) as colorless liquid, LC-MS: 473.3 [MH$^+$].

d) N-[(2S)-1-Cyclopropyl-2-(5-methyl-1,2,4-oxadiazol-3-yl)propan-2-yl]-4-(6-fluoropyridin-3-yl)-5-phenylmethoxypyridine-2-carboxamide 1,1'-Bis(diphenylphosphino)ferrocene palladium (II) chloride (4.24 mg, 5.2 µmol) was added to a mixture of (S)-5-(benzyloxy)-4-bromo-N-(1-cyclopropyl-2-(5-methyl-1,2,4-oxadiazol-3-yl)propan-2-yl)picolinamide (35 mg, 74.3 µmol), 2-fluoro-5-(4,4,5,5-tetramethyl-1,3,2-dioxaborolan-2-yl)pyridine (21.5 mg, 96.5 µmol; CAN 444120-95-0) and 2 M aqueous Cs$_2$CO$_3$ solution (92.8 µL, 186 µmol) in dioxane (700 µL) under an argon atmosphere. The mixture was heated for 8 h to 120° C. in a microwave oven, poured onto ice/1 N HCl and extracted with EtOAc (2×25 mL). The combined extracts were washed with ice/sat. aqueous NaHCO$_3$ solution (25 mL) and ice water/brine (25 mL), dried over Na$_2$SO$_4$ and filtered. The filtrate was brought to dryness and the residue was purified by preparative TLC (silica gel, 2.0 mm, hexanes/EtOAc 1:1) to obtain the title compound (20 mg, 55%) as colorless liquid, LC-MS: 488.4 [MH$^+$].

Example 24

Pharmacological Tests

The following tests were carried out in order to determine the activity of the compounds of formula I:

Radioligand Binding Assay

The affinity of the compounds of the invention for cannabinoid receptors was determined using recommended amounts of membrane preparations (PerkinElmer) of human embryonic kidney (HEK) cells expressing the human CNR1 or CNR2 receptors in conjunction with 1.5 or 2.6 nM [3H]-CP-55,940 (Perkin Elmer) as radioligand, respectively. Binding was performed in binding buffer (50 mM Tris, 5 mM MgCl$_2$, 2.5 mM EDTA, and 0.5% (wt/vol) fatty acid free BSA, pH 7.4 for CB1 receptor and 50 mM Tris, 5 mM MgCl$_2$, 2.5 mM EGTA, and 0.1% (wt/vol) fatty acid free BSA, pH 7.4 for CB2 receptor) in a total volume of 0.2 ml for 1 h at 30° C. shaking. The reaction was terminated by rapid filtration through microfiltration plates coated with 0.5% polyethylenimine (UniFilter GF/B filter plate; Packard). Bound radioactivity was analyzed for Ki using non-linear regression analysis (Activity Base, ID Business Solution, Limited), with the Kd values for [3H]CP55,940 determined from saturation experiments. The compounds of formula (I) show an excellent affinity for the CB2 receptor.

The compounds according to formula (I) have an activity in the above assay (Ki) between 10 nM and 10 µM. Particular compounds of formula (I) have an activity in the above assay (Ki) between 10 nM and 3 µM. Other particular compounds of formula (I) have an activity in the above assay (Ki) between 10 nM and 100 nM.

cAMP Assay

CHO cells expressing human CB1 or CB2 receptors are seeded 17-24 hours prior to the experiment 50.000 cells per well in a black 96 well plate with flat clear bottom (Corning Costar #3904) in DMEM (Invitrogen No. 31331), 1×HT supplement, with 10% fetal calf serum and incubated at 5% CO$_2$ and 37° C. in a humidified incubator. The growth medium was exchanged with Krebs Ringer Bicarbonate buffer with 1 mM IBMX and incubated at 30° C. for 30 min. Compounds were added to a final assay volume of 100 µl and incubated for 30 min at 30° C. Using the cAMP-Nano-TRF detection kit the assay (Roche Diagnostics) was stopped by the addition of 50 µl lysis reagent (Tris, NaCl, 1.5% Triton X100, 2.5% NP40, 10% NaN$_3$) and 50 µl detection solutions (20 µM mAb Alexa700-cAMP 1:1, and 48 µM Ruthenium-2-AHA-cAMP) and shaken for 2 h at room temperature. The time-resolved energy transfer is measured by a TRF reader (Evotec Technologies GmbH), equipped with a ND:YAG laser as excitation source. The plate is measured twice with the excitation at 355 nm and at the emission with a delay of 100 ns and a gate of 100 ns, total exposure time 10s at 730 (bandwidth 30 nm) or 645 nm (bandwidth 75 nm), respectively. The FRET signal is calculated as follows: FRET=T730-Alexa730-P(T645-B645) with P=Ru730-B730/Ru645-B645, where T730 is the test well measured at 730 nM, T645 is the test well measured at 645 nm, B730 and B645 are the buffer controls at 730 nm and 645 nm, respectively. cAMP content is determined from the function of a standard curve spanning from 10 µM to 0.13 nM cAMP.

EC$_{50}$ values were determined using Activity Base analysis (ID Business Solution, Limited). The EC$_{50}$ values for a wide range of cannabinoid agonists generated from this assay for reference compounds were in agreement with the values published in the scientific literature.

In the foregoing assay, the compounds according to the invention have a human CB2 EC$_{50}$ which is between 5 nM and 10 µM. Particular compounds according to the invention have a human CB2 EC$_{50}$ between 5 nM and 1 µM. Further particular compounds according to the invention have a human CB2 EC$_{50}$ between 5 nM and 100 nM. They exhibit at least 10 fold selectivity against the human CB1 receptor in, either both of the radioligand and cAMP assay, or in one of these two assays.

Results obtained for representative compounds of the invention are given in the following table.

In the second column is given the relative efficacy (in %) compared to the reference agonist CP55940 for which this value is set to +100%, measured in analogy to the assay described in Ullmer, C. et al. Functional monoclonal antibody acts as a biased agonist by inducing internalization of metabotropic glutamate receptor 7. Br. J. Pharmacol. 167, 1448-66 (2012). The negative values demonstrate that the compounds of formula (I) are inverse agonists.

| Example | cAMP assay human CB2 EC$_{50}$ [μM] | Percent relative efficacy compared to the reference agonist CP55940 for which this value is set to +100% |
|---|---|---|
| 1 | 0.0152 | −40.1 |
| 2 | 0.2566 | −90.6 |
| 3 | 0.0466 | −85.1 |
| 4 | 0.0144 | −70.5 |
| 5 | 0.0069 | −128.6 |
| 6 | 0.1244 | −102.9 |
| 7 | 0.4971 | −41.7 |
| 8 | 0.0044 | −141.9 |
| 9 | 0.2964 | −114.7 |
| 10 | 1.5551 | −36.8 |
| 11 | 0.1810 | −28.5 |
| 12 | 3.2338 | −40.1 |
| 13 | 0.0261 | −158.8 |
| 14 | 0.0367 | −65.9 |
| 15 | 1.5090 | −75.2 |
| 16 | 0.3147 | −103.1 |
| 17 | 2.0088 | −49.9 |
| 18 | 7.2062 | −48.7 |
| 19 | 0.1479 | 13 |
| 20 | 0.4197 | −150.8 |
| 21 | 0.0870 | −147.5 |
| 22 | 0.0471 | −78.4 |
| 23 | 1.0334 | −87.7 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidone in water. The granulate is then mixed with sodium starch glycolate and magnesium stearate and compressed to yield kernels of 120 or 350 mg respectively. The kernels are lacquered with an aq. solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of Polyethylene glycol 400 and water for injection (part). The pH is adjusted to 5.0 by addition of acetic acid. The volume is adjusted to 1.0 ml by addition of the residual amount of water. The solution is filtered, filled into vials using an appropriate overage and sterilized.

The invention claimed is:
1. A compound selected from the group consisting of:
5-(cyclopropylmethoxy)-4-(2,4-dichlorophenyl)-N-[(2S)-1-hydroxy-4-methylpentan-2-yl]pyridine-2-carboxamide;
4-(4-chlorophenyl)-5-(cyclopropylmethoxy)-N-[(1R,2S)-2-hydroxycyclohexyl]pyridine-2-carboxamide;
4-(4-chlorophenyl)-5-(cyclopropylmethoxy)-N-[(1S,2R)-2-hydroxycyclohexyl]pyridine-2-carboxamide;
methyl 2-[[4-(4-chlorophenyl)-5-(cyclopropylmethoxy)pyridine-2-carbonyl]amino]-2-ethylbutanoate;
methyl 2-[[5-(cyclopropylmethoxy)-4-(3,4-dichlorophenyl)pyridine-2-carbonyl]amino]-2-ethylbutanoate;
4-(4-chlorophenyl)-5-(cyclopropylmethoxy)-N-[(1R,2S)-2-methoxycyclohexyl]pyridine-2-carboxamide;
5-chloro-4-(cyclopropylmethoxy)-N-[(1R)-2-hydroxy-1-phenylethyl]pyridine-2-carboxamide;
5-chloro-4-(cyclopropylmethoxy)-N-[(2S)-3,3-dimethyl-1-(methylamino)-1-oxobutan-2-yl]pyridine-2-carboxamide;
5-chloro-4-(cyclopropylmethoxy)-N-[(2S)-4-methyl-1-(methylamino)-1-oxopentan-2-yl]pyridine-2-carboxamide;
5-chloro-4-(cyclopropylmethoxy)-N-[(2R)-4-methyl-1-(methylamino)-1-oxopentan-2-yl]pyridine-2-carboxamide;
5-cyclopropyl-N-[(2S)-3,3-dimethyl-1-(methylamino)-1-oxobutan-2-yl]-4-[(3-methyloxetan-3-yl)methoxy]pyridine-2-carboxamide;
6-[6-(5-tert-butyl-1,2,4-oxadiazol-3-yl)-4-(cyclopropylmethoxy)pyri din-3-yl]-2-oxa-6-azaspiro [3 0.3]heptane;
tert-butyl (2S)-24[2-(5-tert-butyl-1,2,4-oxadiazol-3-yl)-5-cyclopropylpyridin-4-yl]oxymethyl]pyrrolidine-1-carboxylate;
tert-butyl (3R)-3-[2-(5-tert-butyl-1,2,4-oxadiazol-3-yl)-5-cyclopropylpyridin-4-yl]oxypyrrolidine-1-carboxylate;
5-tert-butyl-3-[5-cyclopropyl-4-[(3-methylsulfonylphenyl)methoxy]pyridin-2-yl]-1,2,4-oxadiazole;

N-[1-(azetidin-3-yl)-1-(5-methyl-1,3,4-oxadiazol-2-yl)ethyl]-5-cyclopropyl-4-(2,2,2-trifluoroethoxy)pyridine-2-carboxamide;

ethyl 2-[[5-cyclopropyl-4-[(3-methyloxetan-3-yl)methoxy]pyridine-2-carbonyl]amino]-2-ethylbutanoate;

5-chloro-N-[1-cyclopropyl-2-(5-methyl-1,2,4-oxadiazol-3-yl)propan-2-yl]-4-[(2,2-difluoro-1-methylcyclopropyl)methoxy]pyridine-2-carboxamide;

4-(benzotriazol-1-yloxy)-N-[1-cyclopropyl-2-(5-methyl-1,2,4-oxadiazol-3-yl)propan-2-yl]-5-(trifluoromethyl)pyridine-2-carboxamide;

N-(4-amino-2-cyclopropyl-4-oxobutan-2-yl)-5-cyclopropyl-4-[(5-fluoropyridin-2-yl)methoxy]pyridine-2-carboxamide; and N-[(2S)-1-cyclopropyl-2-(5-methyl-1,2,4-oxadiazol01-3-yl)propan-2-yl]-4-(6-fluoropyridin-3-yl)-5-phenylmethoxypyridine-2-carboxamide;

or a pharmaceutically acceptable salt thereof.

2. A compound selected from the group consisting of:

5-(cyclopropylmethoxy)-4-(2,4-dichlorophenyl)-N-[(2S)-1-hydroxy-4-methylpentan-2-yl]pyridine-2-carboxamide;

methyl 2-[[5-(cyclopropylmethoxy)-4-(3,4-dichlorophenyl)pyridine-2-carbonyl]amino]-2-ethylbutanoate;

5-chloro-4-(cyclopropylmethoxy)-N-[(2S)-3,3-dimethyl-1-(methylamino)-1-oxobutan-2-yl]pyridine-2-carboxamide;

5-cyclopropyl-N-[(2S)-3,3-dimethyl-1-(methylamino)-1-oxobutan-2-yl]-4-[(3-methyloxetan-3-yl)methoxy]pyridine-2-carboxamide; and N-(4-amino-2-cyclopropyl-4-oxobutan-2-yl)-5-cyclopropyl-4-[(5-fluoropyridin-2-yl)methoxy]pyridine-2-carboxamide;

or a pharmaceutically acceptable salt thereof.

3. A pharmaceutical composition comprising a compound in accordance with claim 1, or a pharmaceutically acceptable salt thereof, and a therapeutically inert carrier.

4. A method for the treatment of pain, neuropathic pain, asthma, osteoporosis, inflammation, psychiatric diseases, psychosis, oncology, encephalitis, malaria, allergy, immunological disorders, arthritis, gastrointestinal disorders, psychiatric disorders rheumatoid arthritis, psychosis or allergy, which method comprises administering an effective amount of a compound of claim 1, or a pharmaceutically acceptable salt thereof, to a patient in need thereof.

5. A pharmaceutical composition comprising a compound in accordance with claim 2, or a pharmaceutically acceptable salt thereof, and a therapeutically inert carrier.

6. A method for the treatment of pain, neuropathic pain, asthma, osteoporosis, inflammation, psychiatric diseases, psychosis, oncology, encephalitis, malaria, allergy, immunological disorders, arthritis, gastrointestinal disorders, psychiatric disorders rheumatoid arthritis, psychosis or allergy, which method comprises administering an effective amount of a compound of claim 2, or a pharmaceutically acceptable salt thereof, to a patient in need thereof.

* * * * *